US006913462B2

(12) United States Patent
Honstein et al.

(10) Patent No.: US 6,913,462 B2
(45) Date of Patent: Jul. 5, 2005

(54) PIN TRAY DENTAL PROSTHESES MODELING SYSTEM WITH RE-USABLE TRAY

(75) Inventors: Jerry P. Honstein, Corona, CA (US); Richard Barnes, Mission Viejo, CA (US); Anthony Siragusa, Anaheim, CA (US)

(73) Assignee: Dental Ventures of America, Inc., Corona, CA (US)

( * ) Notice: Subject to any disclaimer, the term of this patent is extended or adjusted under 35 U.S.C. 154(b) by 197 days.

(21) Appl. No.: 10/461,968

(22) Filed: Jun. 12, 2003

(65) Prior Publication Data

US 2004/0166466 A1 Aug. 26, 2004

Related U.S. Application Data

(63) Continuation-in-part of application No. 10/376,375, filed on Feb. 26, 2003.

(51) Int. Cl.$^7$ .............................................. A61C 11/00
(52) U.S. Cl. ............................. 433/57; 433/34; 433/60; 433/74
(58) Field of Search ........................... 433/34, 74, 213, 433/60, 57

(56) References Cited

U.S. PATENT DOCUMENTS 6,402,513 B1 * 6/2002 Sim ............................. 433/57

* cited by examiner

Primary Examiner—Cary E. O'Connor
Assistant Examiner—Candice C. Stokes
(74) Attorney, Agent, or Firm—William L. Chapin

(57) ABSTRACT

A dental prostheses modeling system includes a re-usable tray having in an upper part thereof a trough for receiving a semi-liquid casting material such as plaster of Paris or die stone, the trough having opposed vertical walls in which are formed alternating vertically disposed ribs and grooves for molding complementary shaped grooves and ribs in opposed sides of the base of a dental model casting molded in said tray. The trough has a base frame which overlies an upwardly concave lower cavity for receiving liquid die stone after the casting base has solidified, hardened and been removed. The base frame has therethrough an elongated aperture joining the upper trough to the lower cavity. A resilient insert is removably lodged in the base frame aperture to form therewith a liquid-tight seal, whereupon liquid die stone is poured into the upper trough to form the base of a dental model casting. After the casting has hardened, the insert is removed, and pins are fitted into selected portions of the cast base. The tray is then inverted to receive liquid die stone which hardens to form a stone base matrix for insertably receiving pins protruding from the casting base. The casting is then severed into segments which are releasably re-engageable along with adjacent portions of the casting within the tray, proper registration between segments of the casting being effected by insertable receipt of pins within holes formed in the matrix during hardening thereof, and engagement between ribs and grooves of the casting segment bases with complementarily-shaped grooves and ribs in the inner side walls of the upper tray trough.

14 Claims, 23 Drawing Sheets

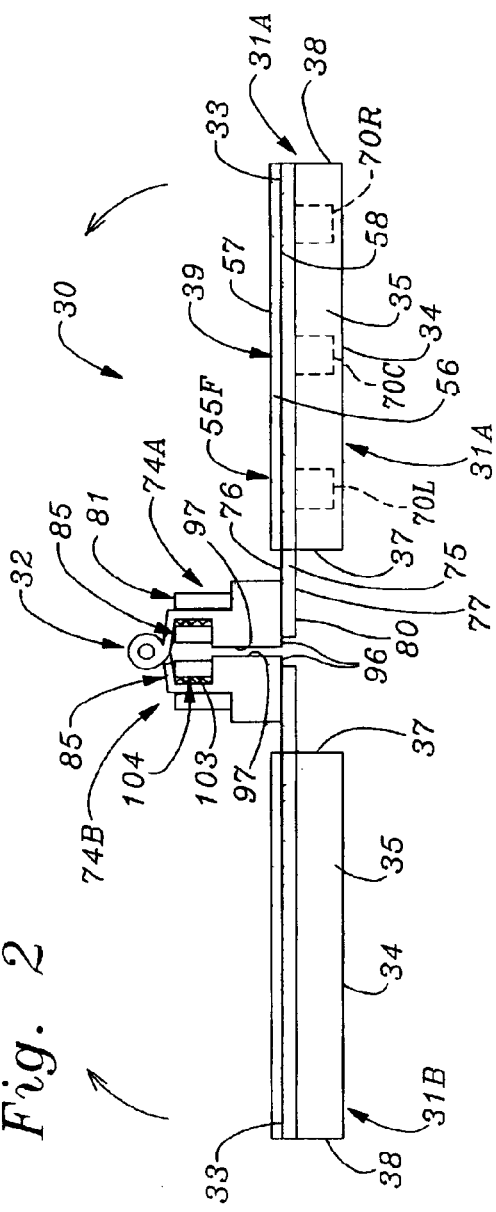
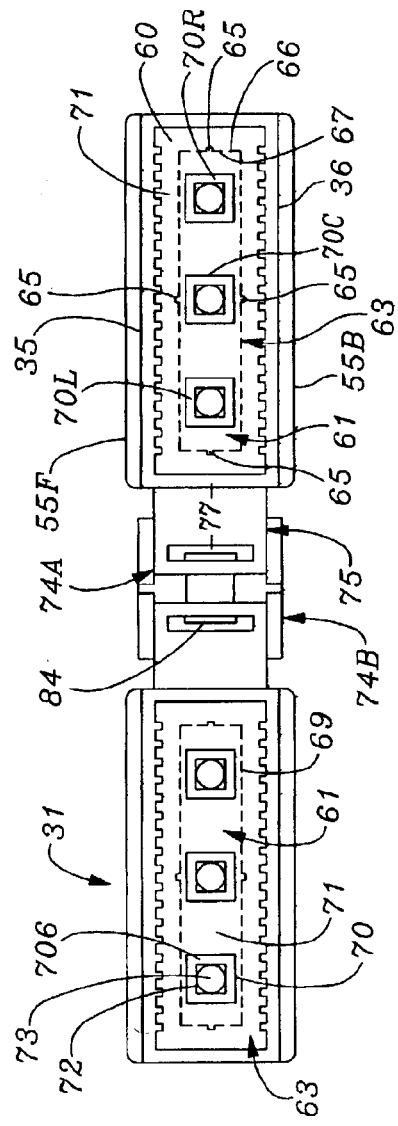
Fig. 2
Fig. 3

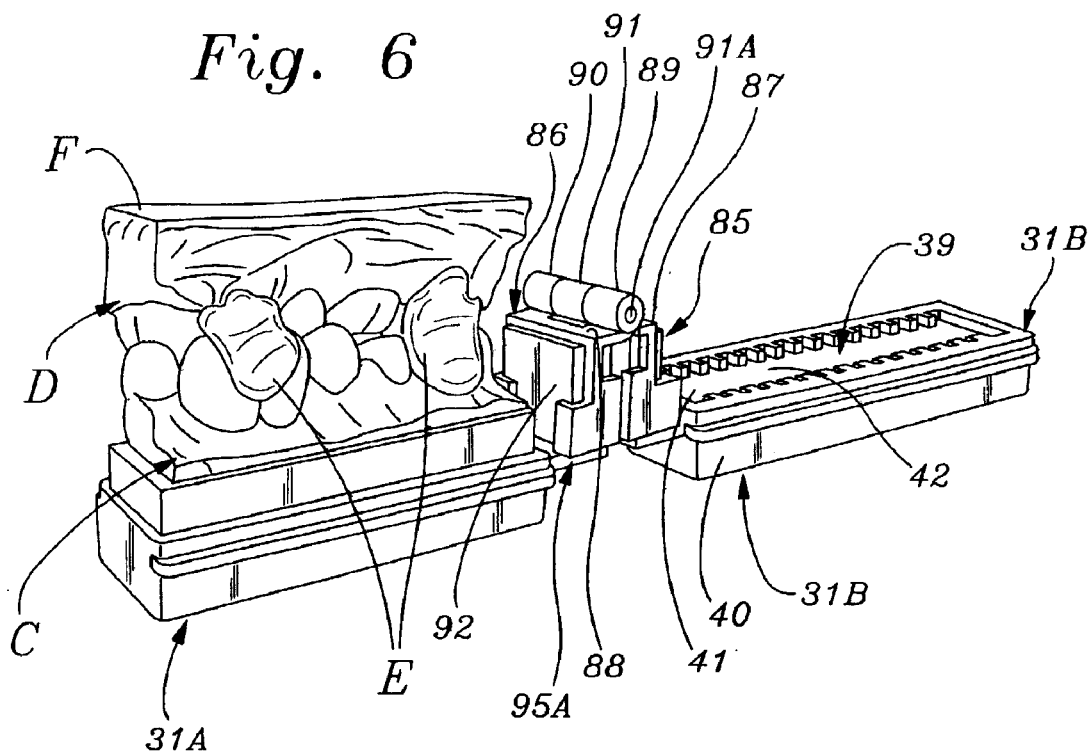
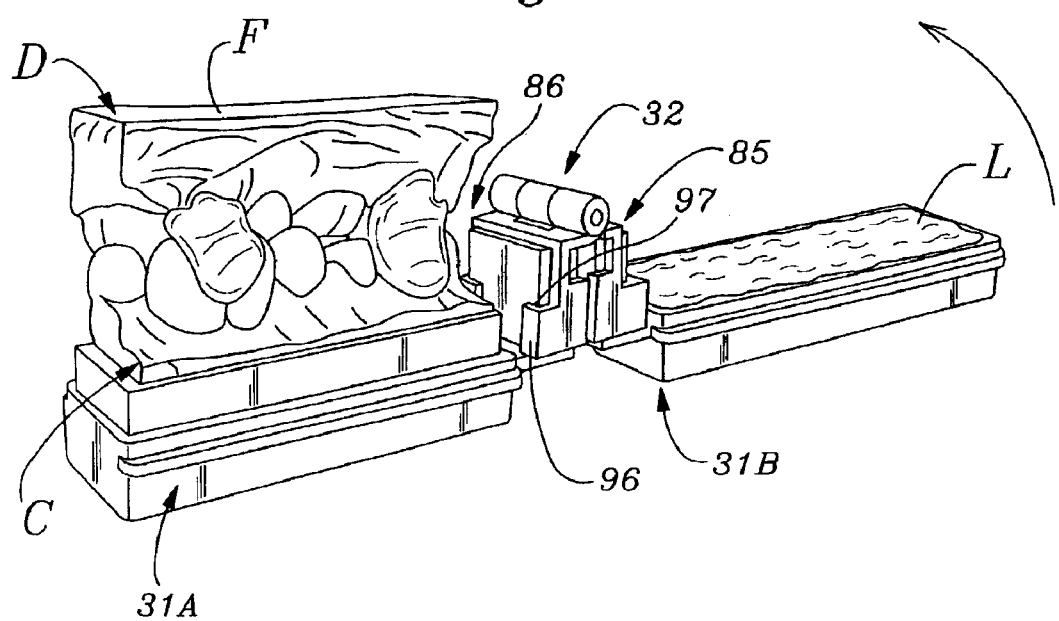

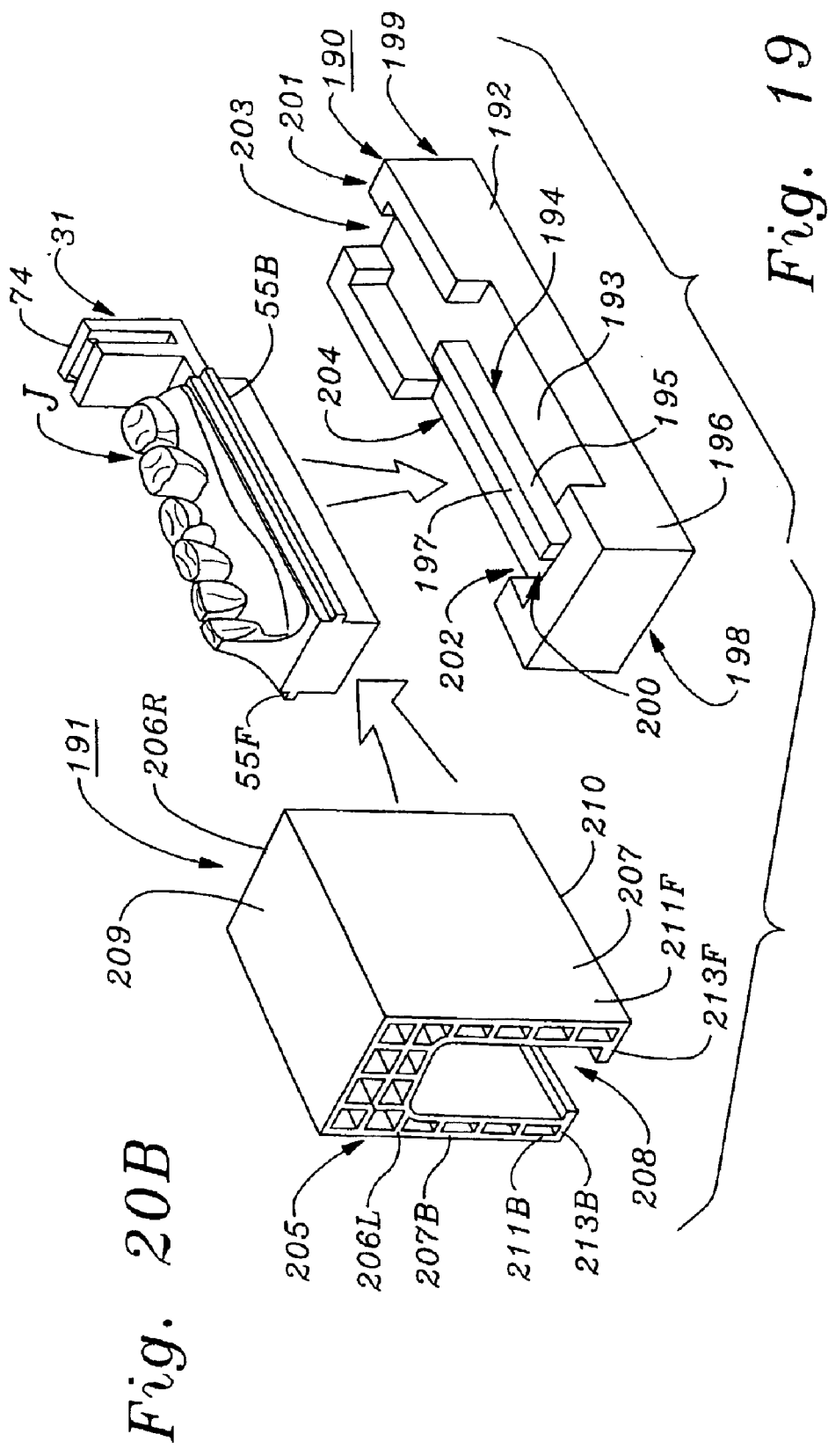

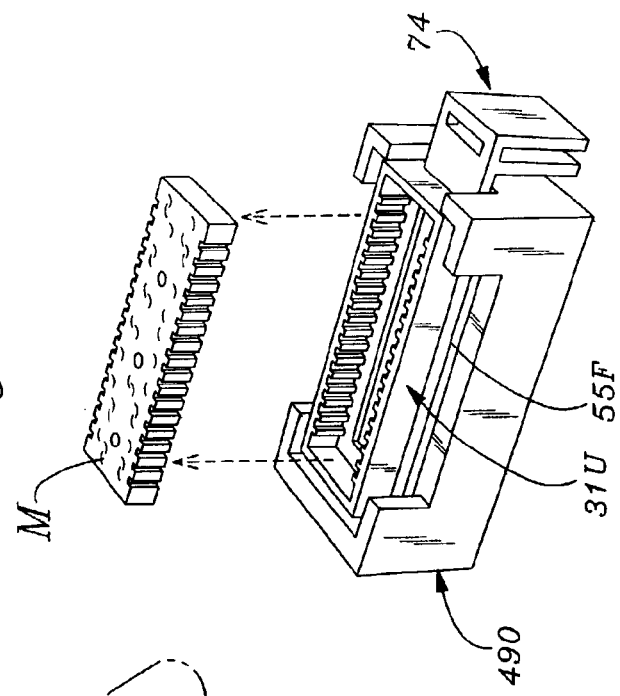
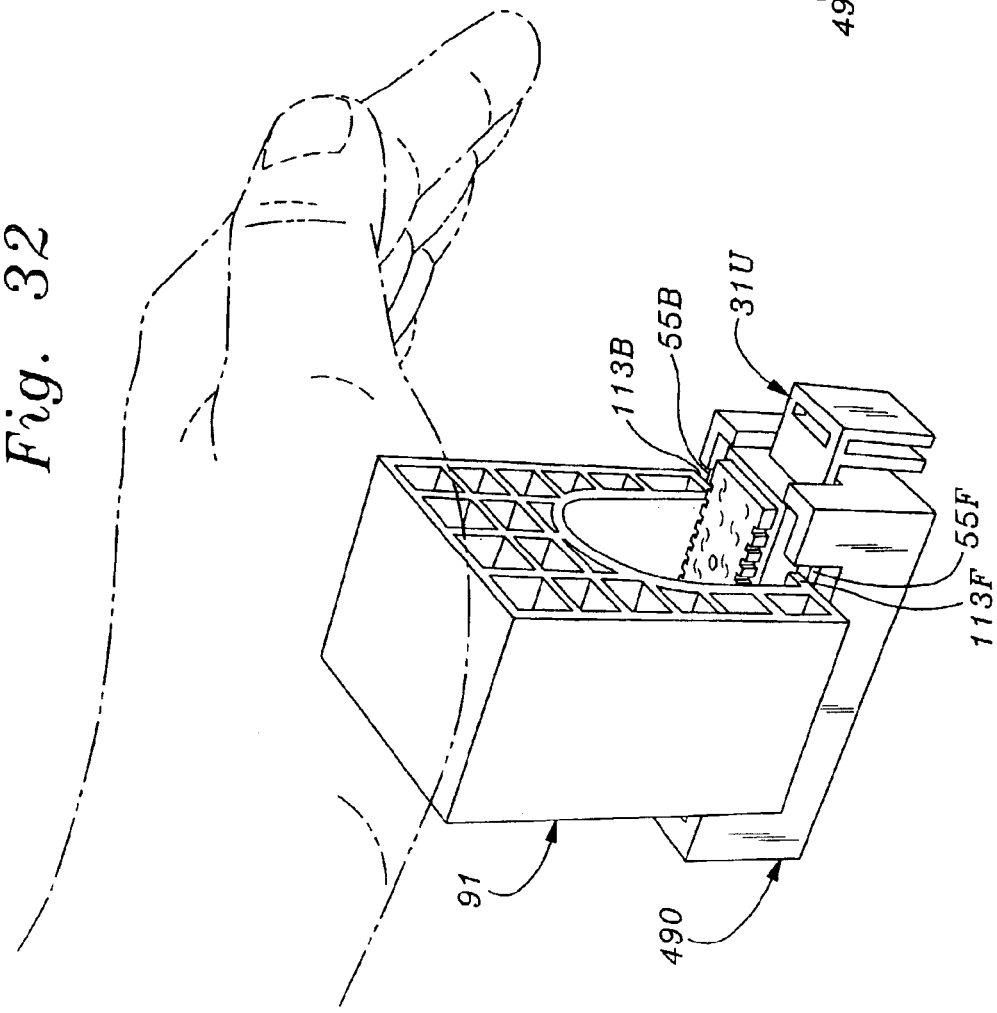

PIN TRAY DENTAL PROSTHESES MODELING SYSTEM WITH RE-USABLE TRAY

RELATED APPLICATION INFORMATION

The present application is a continuation-in-part application of application Ser. No. 10/376,375, filed Feb. 26, 2003.

BACKGROUND OF THE INVENTION

A. Field of the Invention

The present invention relates to articles and methods used in the fabrication of dental prostheses such as crowns and bridges made of various combinations of metal and ceramic materials and used to overlie or replace imperfect or missing teeth. More particularly, the invention relates to a system for use in fabricating crowns and bridges, the system including an apparatus and method for making from a mold or impression of a patient's teeth a dental model cast which is formed from solidified liquid die stone poured into the mold and an upper portion of a tray. The dental model cast is segmentable into die segments, each of which has both horizontally protruding ribs and grooves for releasably engagement with complementary-shaped grooves and ribs formed in the tray, and a pin protruding downwardly from the die segment and adjacent segments for receipt within indexing holes formed through a base member matrix and formed from solidified liquid die stone poured within a lower portion of the inverted tray, the pin facilitating gripping and manipulating of the die during various fabrication operations performed by a dental technician.

B. Description of Background Art

A dental procedure which is routinely used to restore function and aesthetic appearance to a person's mouth after a tooth has become broken, structurally degraded by disease or removed entirely, consists of capping or replacing the tooth with a prosthetic restoration, such as a crown or bridge. One form of dental prosthesis or artificial tooth replacement which is widely used consists of a cap or crown for a tooth that is made of a resin, molded ceramic material, a precious metal such as gold or an alloy thereof, or a layered combination of metals and resins or ceramic materials. Various combinations of the foregoing materials provide tooth restorations which possess requisite durability and aesthetic appearance, as well as sufficient hardness to be suitable for chewing foods. The process of fabricating tooth restorations has been in use for a substantially long time, and includes a well-defined sequence of steps, which are briefly summarized below.

According to a first step in existing methods of fabricating dental prostheses or artificial replacement teeth, a negative impression mold is made of a group of a patient's teeth, including missing, broken or decayed teeth which are to be repaired or replaced and teeth which are laterally adjacent to the defective teeth. Such impressions are typically made by positioning within the mouth of a patient, adjacent to teeth to be restored, a shallow curved tray which contains a polymer material such as alginate, elastomer, hydrocolloid or a polyether, which is capable of being indented by a tooth, and forming and retaining a stable impression of the tooth. The impression material is initially in the form of a putty, slurry or thick paste which rapidly solidifies at ambient room temperature and pressure. The tray is inserted into a patient's mouth positioned generally horizontally and in vertical alignment with a subject area of the teeth, and the patient bites down on the tray, or the tray is pressed into contact with the teeth, thus pressing the teeth into the viscous semi-liquid mold impression material held by the tray. After a few minutes, the mold impression material solidifies into a rubber-like elastomeric state which has formed therein precise negative impressions of teeth in a subject area of the patient's mouth.

Dental impression trays for use as described above are available in a variety of styles. One type tray has an arcuately curved plan-view shape which is similar to the curved arrangement of teeth in the jaw. The curved arc length of the tray approximates that of about one half an upper or lower jaw and hence is referred to as a quadrant tray. A flat, paddle-like handle protruding horizontally outwards from one end of the tray is usually provided, to facilitate inserting and removing the tray from a patient's mouth. A typical quadrant tray has on one side thereof a curved trough for receiving impression mold material, may be used to make impressions of upper or lower jaw quadrants and is referred to as a standard quadrant or single-bite tray.

Since an important structural feature of a dental prosthesis is proper registration and biting contact or occlusion between the prosthesis and teeth located in the opposing jaw, it is desirable to make an impression of occluding teeth in the opposing jaw in addition to the impression made of teeth that are to be restored. Therefore, it has been a trend in dentistry for the dental professional to simultaneously make impressions of teeth that are to be restored and occluding teeth in the opposing jaw. A convenient method for simultaneously making restorative and opposing impressions utilizes a tray which has a plan-view shape similar to that of a single-bite, standard quadrant impression tray, but which has upper and lower troughs for holding mold impression material in both upper and lower sides of the tray. Both the upper and lower troughs of these "double-bite" or "triple" trays are filled with viscous impression material and inserted into the patient's mouth between the upper and lower jaws in vertical alignment with teeth to be restored, whereupon the patient bites down on the tray, simultaneously forming impressions of upper and lower teeth.

After impressions of teeth have been made in the manner described above, and the mold impression material solidified, the tray holding solidified mold impression material containing negative impressions of a patient's teeth is removed. The mold, typically referred to as an "impression," is then used to make positive replicas of teeth by pouring a semi-liquid molding material such as plaster of Paris, or die stone, into the depressions formed in the impression, which are accurate negative replicas of the teeth. After the die stone has solidified into a hard stone-like casting, or cast, the cast is removed from the impression, a task which is facilitated by the fact that the impression material is elastomeric, enabling it to be readily peeled away from the die. The casting is then used to fabricate one or more tooth restorations or prostheses in the following manner.

A master cast, i.e., a cast which includes replicas of teeth which are to be restored, is partitioned into one or more individual segments and/or dies, each consisting of a replica of a tooth which is to be replaced by or fitted with a dental prosthesis. Partitioning of a master cast into die segments is typically accomplished by making parallel vertical saw cuts through the master cast. The individual die segment or segments are then used as three-dimensional models or templates for fabricating crowns or bridges. In general, the exterior surfaces of the prosthesis cannot simply replicate those of the die segments. This is because the occlusal surface of the prosthetic tooth restoration, and to a lesser extent, lateral surfaces of the restoration, may require contouring which is different from that of the die segment. For example, the process of fabricating crowns for diseased or damaged teeth entails grinding decayed or broken outer portions of the tooth down until a stump of healthy dentin or enamel remains, a procedure referred to as "prepping" the tooth. Obviously, a crown which is fabricated to fit onto a stump must have a substantially different, tooth-like shape rather than a stump-like shape.

From the foregoing discussion, it can be appreciated that the fabrication of dental prosthesis models from die segments is a labor-intensive task requiring the skills of a prosthodontist or skilled, experienced, dental lab technician. Fabrication of prosthetic dental models typically requires that die segments be contoured by applying a workable material to exterior portions of the die segment, and sculpting the material. The die segment is then replaced into the space in the master cast from which it has been removed, and proper occlusion of the sculpted prosthetic model confirmed by bringing model teeth replicated in the opposing cast into bite-like contacting registration with the occlusal surfaces of the prosthetic model and adjacent teeth replicas of the master cast. This registration check, generally must be repeated several times, to ensure proper sculpting of the occlusal surface of the die segment which serves as a model for fabricating a dental prosthesis. Moreover, it is essential that the biting contact or occlusion between the teeth replicated by the master cast and opposing cast precisely duplicate occlusion of the patient's teeth. Therefore, the master cast and opposing cast must be precisely and repetitively pivotably contacted against one another in a motion which simulates the opening and closing of a patient's jaws. Upon satisfactory completion of sculpting of lateral and occlusal surfaces of die segments, the die segment is used as a mold pattern for casting a metal, ceramic, or metal-ceramic composite dental prosthesis.

One type of device which is used to pivotably register master and opposing dental models or arches is referred as an articulator. For example, Cho, U.S. Pat. No. 6,019,601, Tray Modeling System With Articulator Assembly And Ejection Mechanism For Producing A Dental Model, discloses a pair of trays which are removably and pivotably joined together by detachable hinge members. Each tray has formed upon an upper surface thereof a rectangularly-shaped, trough-like depression, the longest inner facing side walls of the trough having formed therein alternating vertically disposed ribs and grooves. The device is used by pouring a thick paste of liquid die stone slurry into both a dental impression and the tray, and inverting the impression to enable the liquid die stone slurries in the impression and tray to commingle. When the die stone has solidified, the impression is removed from the cast, and the cast removed from the tray by punching through a frangible base panel in the tray, forcing the cast vertically outwards from the trough. The cast is then sawed into segments, which are returnable to precisely repeatable locations within the trough because of the interlocking ribs and grooves formed in the vertical walls of the cast by die stone solidifying in the grooves and ribs, respectively, of the trough side walls, during hardening of the die stone. In the same manner, an opposing cast is made in the other tray, and the trays pivoted towards one another on the hinge pins to precisely and repeatedly bring the occlusal surfaces of the opposing cast and master cast into occlusal registration.

The Cho modeling system and articulator provides a convenient means for preparing and articulating dental models. However, some dental technicians prefer working with die segments which have an elongated cylindrical pin protruding from the base of the die segment. In modeling systems using pinned die segments, the pins are insertably received in holes provided in the base of a tray, and are used to reproducibly position or relate individual die segments to adjacent portions of the master cast. Moreover, a pin protruding from a die segment provides a convenient handle which enables the dental technician to hold a die segment while working on it, including rotating the die segment a full 360 degrees by twisting the die segment pin between the thumb and forefinger of the dental technician. Thus, Sim, U.S. Pat. No. 6,402,513, Dental Model Articulator, discloses a dental model articulator which has pinned die segments. The dental model articulator disclosed in Sim utilizes a top insert which has front and rear upwardly protruding ridges that have grooved upper surfaces. The insert is detachably supported on a lower frame. To pour a master cast of a dental impression, a middle frame must be fastened to a lower frame and around the top insert by engaging slots on left and right sides of the middle frame with retentive latches which protrude upwards from the lower frame, on left and right sides of an upper opening in the lower frame which holds the top insert. According to the disclosure of Sim, the middle frame is discarded after completion of a second pour of liquid die stone through a bottom opening of lower frame, to form a perforated matrix for receipt of pins installed in the base of the first impression casting. The grooved insert is discarded after the first pour.

The present invention was conceived of to provide an improved dental prostheses modeling system which utilizes die segments which each have ribs and grooves for repeatable removal from and re-registration within a cast, as well as a downwardly protruding pin for facilitating both manipulation of the die segment and reinsertion into the cast, the die segment being quickly and easily fabricated using a sparse number of components and steps.

OBJECTS OF THE INVENTION

An object of the present invention is to provide a dental prostheses modeling system for fabricating models of human teeth from impressions made thereof.

Another object of the invention is to provide a dental prostheses modeling system which includes a tray having in an upper part thereof a trough for receiving a semi-liquid modeling material or casting material such as plaster of Paris or die stone, the trough having opposed vertical walls in which are formed alternating vertically disposed ribs and grooves for forming a casting, a base portion of which has in outer walls thereof alternating vertically disposed grooves and ribs, the trough having a frangible base plate which overlies an upwardly concave cavity for receiving liquid die stone after the upper casting has solidified, hardened and been removed, the base plate being broken and removed to uncover an elongated aperture joining the upper trough to the lower cavity, enabling the casting to be pushed upwardly out of the tray, pins fitted into selected portions of the casting base, the castings reinserted into the trough, and the tray inverted to receive liquid die stone which hardens to form a stone base matrix for insertably receiving pins protruding downwardly from portions of the casting, the casting being then removed from the trough in the upper portion of the tray and severed into segments which are releasably re-engageable along with adjacent portions of the casting within the tray, proper registration between segments of the casting being effected by insertable receipt of pins within holes formed in the die stone base during hardening thereof, and engagement between ribs and grooves of the casting segments with complementarily-shaped grooves and ribs in the inner side walls of the upper tray trough.

Another object of the invention is to provide a dental prostheses modeling system which includes a pair of upper and lower trays for use in molding from solidified liquid die stone bases for cast dental models of upper and lower teeth from impressions thereof, the trays being hingedly joinable to enable master and opposing dental castings formed in the trays to pivotably contact one another to ascertain proper occlusion between surfaces of teeth modeled by the master and opposing casts, each tray having in an upper part thereof a trough having formed in inner facing walls thereof alternating inwardly projecting ribs and grooves, the trough having a frangible base plate which may be pushed upwardly to cause it to break and eject a hardened dental model casting base from the tray, whereupon vertically downwardly disposed pins may be installed in the bases of selected segments of the casting, the casting replaced in the trough with the pins, now coated with a release agent, protruding downwardly through the opening left by removal of the frangible base plate, and liquid die stone poured into a concave lower portion of the inverted tray to form upon hardening a base stone matrix having holes formed through its thickness dimension by the pins, whereupon the casting may be removed from the upper trough portion of the tray, and segmented by vertical cuts into a desired number of die segments each having a pin protruding downwardly from its base, and the die segments releasably replaced in the tray in precise relative relationship because of indexing provided by the die segment pins being insertably received in corresponding hoes in the base die stone matrix, and engagement between vertically disposed ribs and grooves molded in the sides of the casting with corresponding grooves and ribs in the inner facing walls of the trough.

Another object of the invention is to provide a dental prostheses modeling system which includes a re-usable modeling tray for molding from solidified liquid die stone a cast dental model having a base which has protruding from outer wall surfaces thereof ribs which alternate with grooves, for releasably engaging complementary grooves and ribs within inner walls of the tray, and which has protruding from a lower wall surface of the casting base pins for releasable engagement with bores formed in a matrix plate cast in a lower portion of the tray.

Various other objects and advantages of the present invention, and its most novel features, will become apparent to those skilled in the art by perusing the accompanying specification, drawings and claims.

It is to be understood that although the invention disclosed herein is fully capable of achieving the objects and providing the advantages described, the characteristics of the invention described herein are merely illustrative of the preferred embodiments. Accordingly, we do not intend that the scope of our exclusive rights and privileges in the invention be limited to details of the embodiments described. We do intend that equivalents, adaptations and modifications of the invention reasonably indexable from the description contained herein be included within the scope of the invention as defined by the appended claims.

SUMMARY OF THE INVENTION

Briefly stated, the present invention comprehends a system which includes an apparatus and method for fabricating models of human teeth; the models are subsequently used in the fabrication of dental prostheses such as crowns and bridges made of various combinations of metal and ceramic materials and used to overlie or replace imperfect or missing teeth. According to the invention, methods and apparatus are provided for making dental impression casts which are segmentable into die segments for use as models in fabricating dental prostheses.

According to one aspect of the invention, a molding tray for molding the base of a dental model cast has a longitudinally elongated rectangular plan view shape, and has formed in opposed inner vertically disposed longitudinal perimeter walls thereof horizontally outwardly protruding protrusions alternating with horizontally inwardly protruding depressions. Complementary-shaped depressions and protrusions are formed in opposed inner facing walls of the base of a dental model cast formed from solidified liquid die stone poured into the tray, thus forming with vertical perimeter walls of the tray upper and lower shallow, rectangular plan view upper and lower depressions or troughs. According to the invention, the tray includes a horizontally disposed, frangible base plate which is located between upper and lower surfaces of the tray. The frangible base plate serves as a support base for pouring a base for a dental model casting within the upper trough in the upper portion of tray. Semi-liquid die stone is poured to overflowing into a dental impression mold containing imprints of a patient's teeth and poured to overflowing into the upper opening of the upper trough in the upper portion of the tray. The filled impression is then inverted, positioned over the tray, and pressed down into semi-liquid die stone in the tray. The liquid die stone in the impression and tray co-mingle, eventually hardening to form a unitary cast comprising a base portion molded in the tray and an upper portion which replicates teeth which imprinted the impression mold. After the cast has hardened, an upwardly directed force is exerted on the underside of the frangible base plate, breaking the base plate and ejecting the hardened cast upwardly out of the tray. The hardened cast is then inverted, and blind bores are drilled into the lower surface of the inverted base of the cast, the bores being positioned in vertical alignment with cast replicas of selected teeth which are to serve as models for fabricating individual prostheses. Cylindrically-shaped pins are then inserted into the bores, and the cast is then flipped over to an upright position, with pins protruding perpendicularly downwards from the base of the cast, and reinserted into the upper opening of the tray. Ribs and grooves molded into opposite longitudinally disposed vertical sides of the cast base vertically slidably engage with complementary-shaped grooves and ribs in the inner side walls of the tray which formed the ribs and grooves of the cast. This arrangement ensures that the cast is returned to a previously predetermined lateral index position relative to the horizontal tray perimeter. Moreover, the cast is returned to a previously predetermined vertical position within the tray by abutting contact between the lower surface of the base of the cast and a flat rectangular ring-shaped upper edge wall of the tray. The tray and inserted cast are then inverted, with the casting secured from falling out of the tray by a preferred method described below. Liquid die stone is then poured into the lower opening of the lower trough in the lower portion of the tray to a level between the lower edge of the tray and the downwardly protruding ends of the indexing pins, which are coated with a liquid release agent before pouring the die stone. Liquid die stone within the lower tray trough is then allowed to harden, forming a stone base matrix. An upwardly directed force is then exerted on the bottom surface of pins protruding from the stone base matrix, thereby pushing the cast upwardly out of the tray. The cast is then segmented into individual die segments for modeling individual dental prostheses, by making one or more saw cuts vertically through the cast, adjacent to a selected die segment. Individual die segments are once again reinserted into the upper opening of the tray, to thereby re-assemble a complete cast comprised of individual die segments and adjacent portions of the cast within the tray. Placement of the pinned die segments within the tray is facilitated by initial approximate alignment of mating ribs and grooves in the inner sides of the tray and the outer sides of the die segment effected by partial insertion of a die segment pin into the upper opening of a corresponding pin bore through the stone base matrix in the lower part of the tray. The combined aligning forces provided by insertion of a pin into a pin bore, and subsequent insertion of ribs of the casting base into tray grooves, enables individual die segments to be quickly and easily removed from the tray, subjected to various prosthesis modeling operations, and returned to a precisely repeatable, indexed position within the cast, as many times as is required.

A preferred embodiment of a pin tray modeling system according to the present invention includes an opposing tray for making a casting of a dental impression which was made of teeth opposed to those which are to be fitted with prostheses. The preferred embodiment also includes components which hingedly couple a master tray holding a master impression cast to an opposing tray holding an opposing impression cast and forming therewith an articulator mechanism which enables the occlusal surfaces of the master and opposing casts to be brought into pivotable contact with one another, thereby simulating closure of a patient's jaws and proper occlusion of the teeth modeled in the two casts. If dental prostheses are required only for one jaw, the cast made of the opposing jaw does not have to have removable die segments. Therefore, the opposing tray need not be provided with the previously described structural features which enable die segments to be removed and replaced within the tray. However, to minimize the number of different type parts required by the present system, the opposing tray may be constructed identically to the master tray, even though the frangible base and indexing grooves and ribs are not required for the opposing cast, since it may remain permanently affixed to the tray.

In any event, both the master and opposing trays, which may be of identical construction, are provided with a hinge coupler bracket which extends longitudinally outwards from a short end of each tray. The bracket has the shape of a bifurcated L-bracket including a flat longitudinally disposed horizontal floor plate which extends perpendicularly outwards from a short vertical end wall of the tray. The floor plate of the bracket has a flat horizontally disposed upper surface which is recessed slightly below the upper surface of the perimeter edge wall of the tray. A pair of rectangularly-shaped connector plates protrudes upwardly from an outer longitudinal end portion of the floor plate. The outer connector plates from a pair of trays are releasably joined together by a hinge coupler member that has an upper piano-type hinge, and opposed horizontal upper support plates located on opposite sides of a horizontally disposed hinge pin. The hinge coupler has protruding perpendicularly downwardly from outer ends of each support plate a vertical connector plate which has at the lower end thereof a pair of inwardly facing C-shaped channel members which have therein opposed vertically disposed C-shaped channels adapted to insertably receive an outer upstanding end plate of a tray coupler. This construction enables the outer slotted ends of the hinge coupler to be readily slipped removably over the upstanding connector flange plates of a longitudinally aligned pair of trays, i.e., a master tray and an opposing tray, and thereby hingedly coupling the two trays together so that upper surfaces of the trays may be pivoted towards and away from one another to simulate closure and opening of a patient's jaws.

According to the present invention a pin tray dental prostheses modeling system preferably utilizes a re-usable modeling or molding tray for fabricating cast dental models. A re-usable molding tray according to the present invention is substantially identical in construction to the molding tray described above, but does not have a frangible center panel located between upper and lower surfaces of the tray. The re-usable molding tray has instead of a frangible center panel a rectangular ring-shaped base wall which has through its thickness dimension a rectangularly-shaped aperture. Thus constructed, the re-usable tray according to the present invention can be fabricated as an injection molded part, or by removing the center panel from a tray constructed as described above.

A dental modeling system with re-usable pin tray according to the present invention also includes a re-usable resilient insert which has a rectangular plate-shaped base and rectangular lug which protrudes upwardly from the base, the lug being adapted to be resiliently inserted upwardly from a lower opening in the tray into the aperture through the base wall of the tray.

The lug has a flat upper surface located at a height above the upper surface of the insert base plate such that when the lower edge wall of the tray is seated on the upper surface of the insert base plate, the upper surface of the lug is parallel to the base plate and is substantially flush with the upper surface of the rectangular ring-shaped base wall of the tray. The lug fits within the tray aperture in a resilient liquid-tight seal, thus forming with adjacent inner side walls of the upper portion of the tray a rectangular box-shaped trough which serves as a mold for receiving liquid die stone to form the base of a dental model cast. After liquid die stone has hardened to form a cast, the insert is withdrawn from the tray aperture and the lower trough in the tray. The tray and cast are then processed by any of the various methods discussed above for the tray provided with a frangible base plate, to fabricate individual pinned die segments comprising individual dental prostheses models which are repeatably removable and returnable to precisely pre-determined index positions within a cast held in the tray.

BRIEF DESCRIPTION OF THE DRAWINGS

FIG. 2 is a side perspective view of a pair of trays of the type shown in FIG. 1, the trays being joined by a hinge coupler.

FIG. 3 is a lower plan view of the trays and coupler of FIG. 2.

FIG. 6 is a perspective view showing a completed master dental model casting residing in a first tray in which it was cast, an opposing cast positioned above the master cast with occlusal surfaces of upper and lower replica teeth in the opposing and master casts temporarily adhered together in proper occlusal registration by blobs of wax, and the first, master tray coupled to a second, opposing tray by a hinge coupler.

FIG. 7 is a view similar to that of FIG. 6, but showing semi-liquid die stone applied to both the upper surface of the opposing cast, and the upper surface of the opposing tray.

FIG. 19 is a perspective view of a knock-out template for removing a frangible base plate of the tray shown in FIGS. 1–3.

FIG. 20B is a side perspective view of the tool of FIG. 20A.

FIG. 32 is a perspective view showing a knock-out tool being used to eject a die stone base matrix from the tray of FIG. 31.

FIG. 33 is a perspective view showing a molding tray with die stone base matrix ejected, thus preparing the tray for re-use.

DESCRIPTION OF THE PREFERRED EMBODIMENTS

A. Drawing Description Summary

Figure 20A:
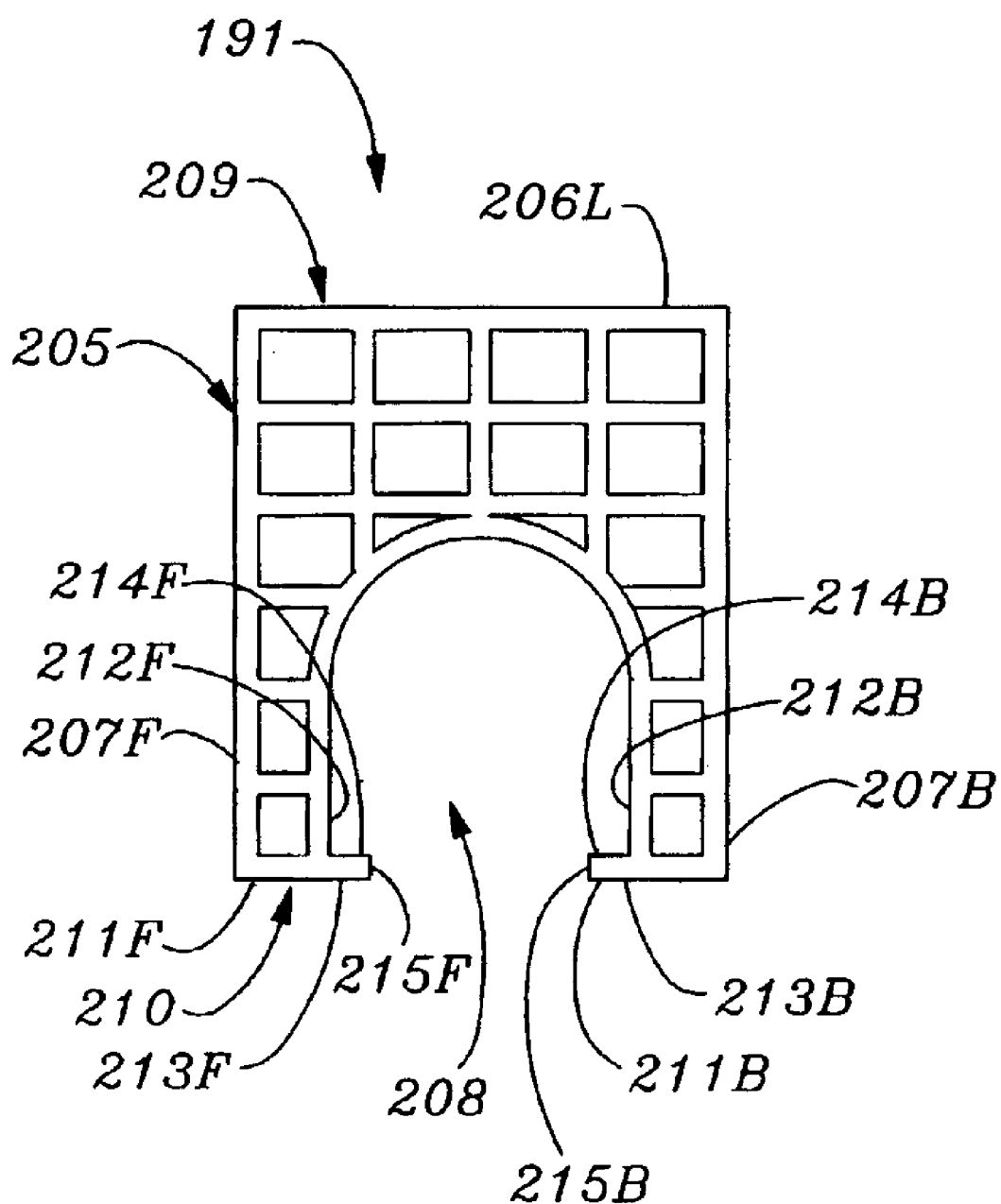
FIG. 20A is a side elevation view of a knock-out tool useable with the template of FIG. 19 to remove a frangible base plate from the tray of FIGS. 1–3.
Figure 21:
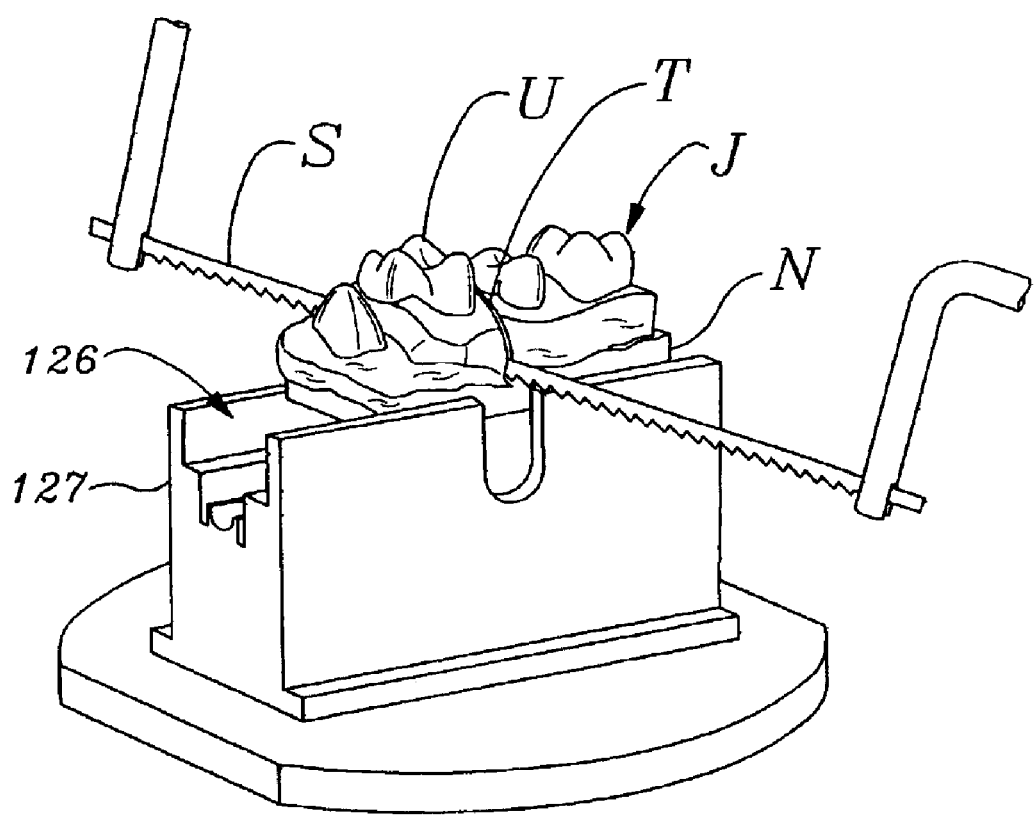
FIG. 21 is a perspective view of a sawing stand for use in segmenting a dental model cast according to a method of the present invention.
Figure 22:
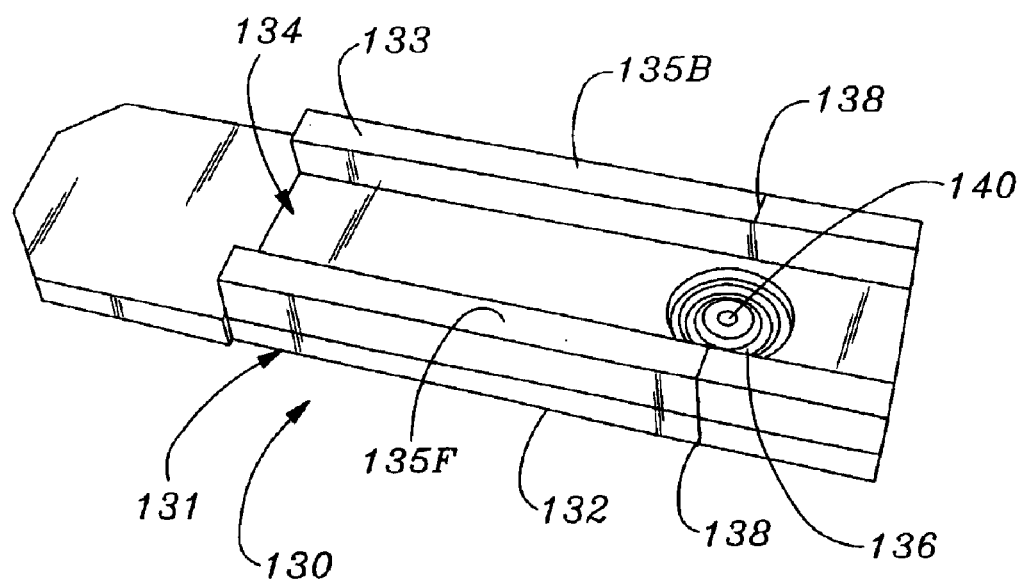
FIG. 22 is a perspective view of a drilling alignment fixture comprising a component for use in an alternative embodiment of a pin tray dental prostheses modeling system according to the present invention.

FIGS. 1–3 and 19–21 illustrate components of a basic embodiment of dental prostheses modeling system according to the present invention, while FIG. 22 illustrates a drilling alignment fixture for use in an alternate embodiment of the system.

FIGS. 4–8 illustrate steps in a method of making a dental model cast from a single quadrant impression for use in fabricating dental prostheses, according to a basic embodiment of the invention.

Figure 9:
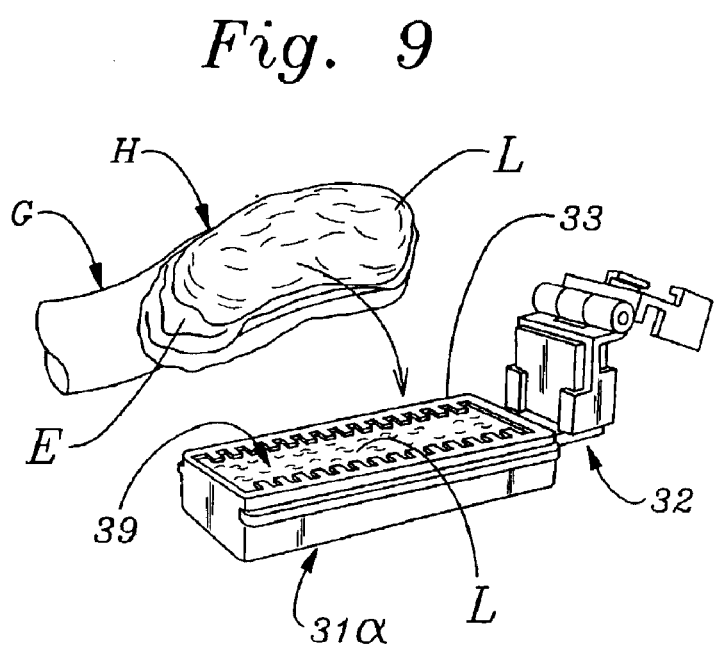
FIG. 9 is a perspective view showing a first step in a method of making a master dental model cast and an opposing cast from master and opposing impression molds made of teeth in opposite jaws of a patient by a double-bite or "triple" impression tray.
Figure 10:
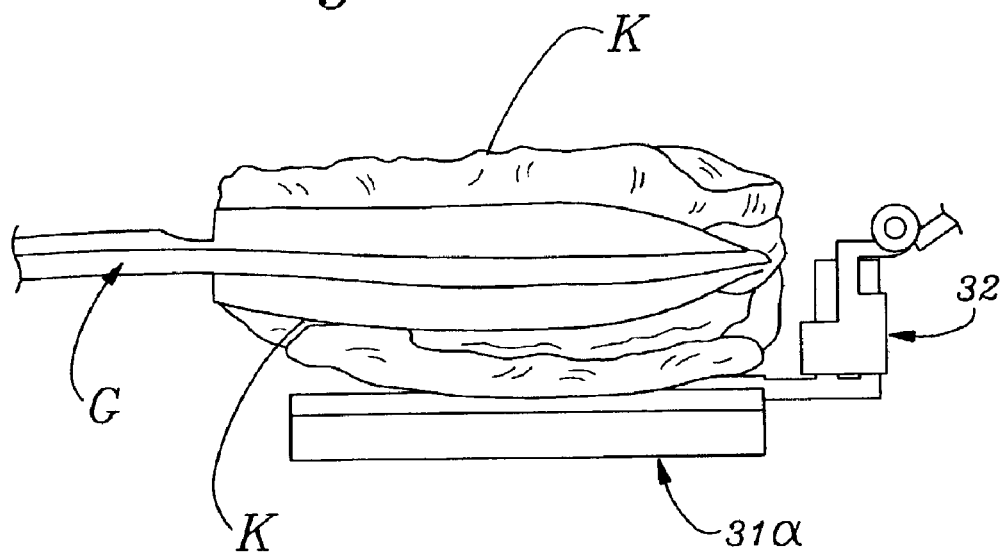
FIG. 10 is a perspective view of a second step in fabricating master and opposing articulated casts according to the present invention.
Figure 11:
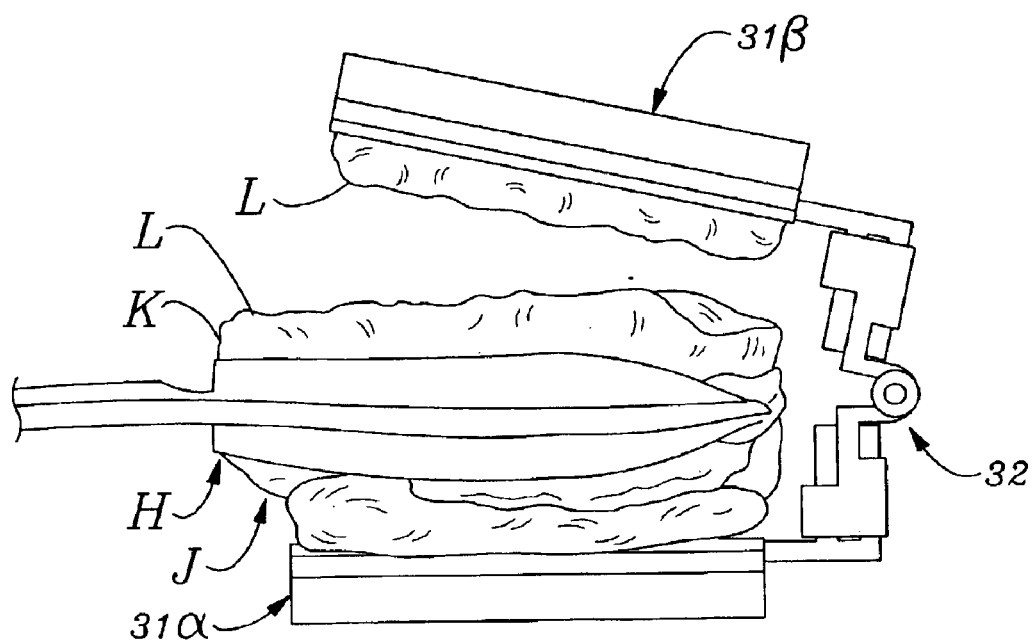
FIG. 11 is a perspective view of a third step in the method of FIG. 10.

FIGS. 9–11 illustrate preliminary steps in making master and opposing dental model casts from master and opposing mold impressions made by teeth in upper and lower jaws of a patient, use a "double-bite" or "triple" impression tray.

FIGS. 12–15 illustrate further steps in the method of fabricating a dental prostheses model according to the present invention, from either a single-bite or double-bite impression.

Figure 17:
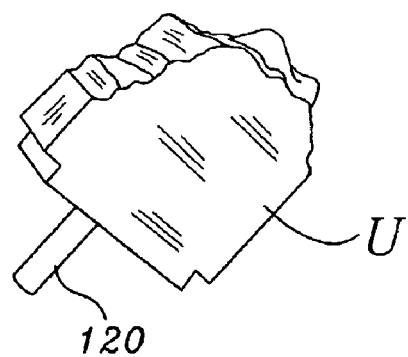
FIG. 17 is a fragmentary view of the article of FIG. 16 on an enlarged scale, showing a die segment thereof.
Figure 16:
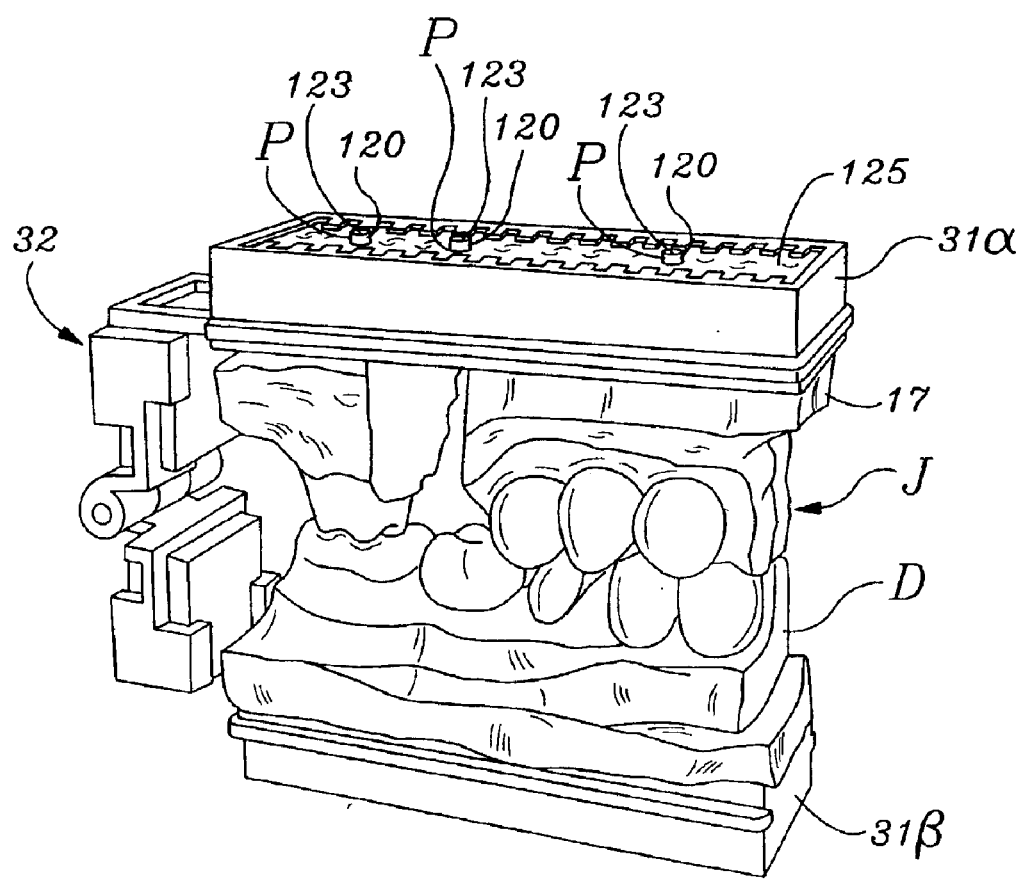
FIG. 16 is a perspective view of a completed articulatable model of a pair of master and opposing dental modeling system casts fabricated using the method and apparatus according to the present invention.
Figure 18:
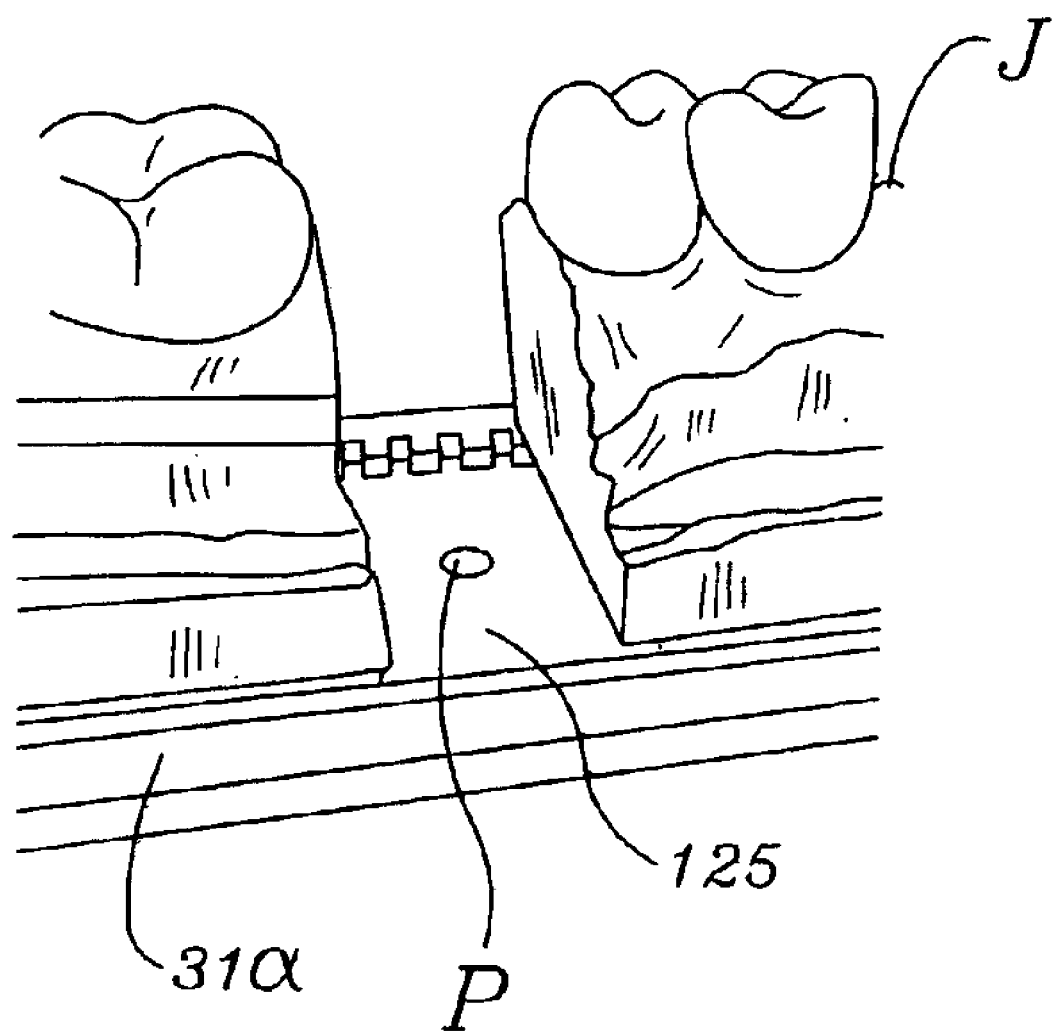
FIG. 18 is another fragmentary view of the article of FIG. 11 on an enlarged scale, showing part of a master cast with the die segment of FIG. 17 removed from the cast.

FIGS. 16–18 illustrate a finished pair of dental prostheses model casts mounted in an articulator according to the present invention.

FIGS. 19–21 illustrate tools for use in practicing the present invention.

FIGS. 22–27 illustrate an alternative apparatus and method for making dental model casts according to the present invention.

FIGS. 28–38 illustrate the construction and use of a re-usable tray and insert according to the present invention.

B. Detailed Description

Figure 1:
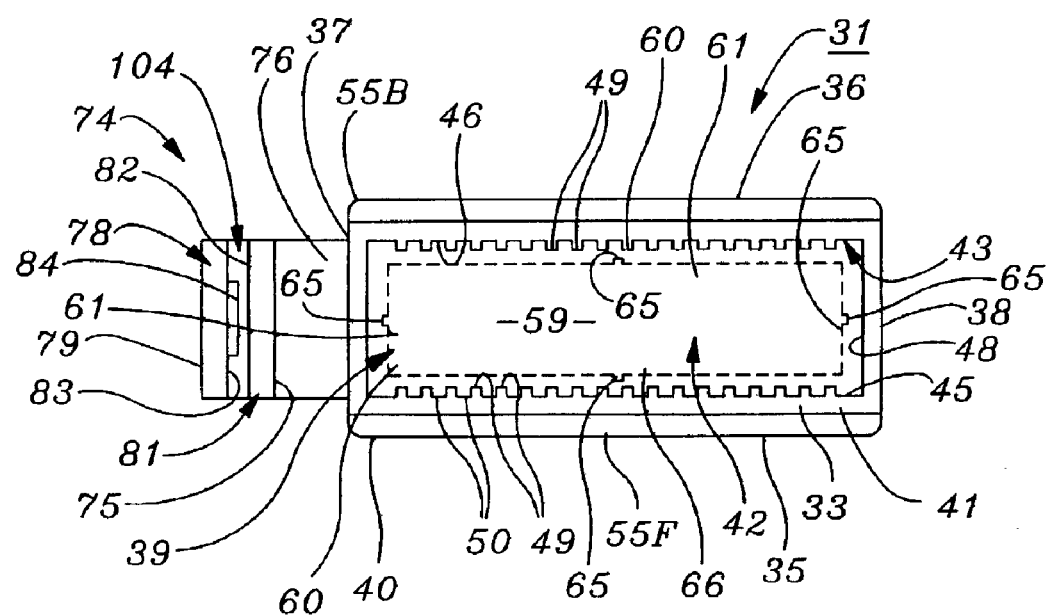
FIG. 1 is an upper plan view of a pin tray for a dental prostheses modeling system according to the present invention.

Referring now to FIGS. 1–3, an apparatus 30 for making pin-tray dental prostheses models according to the present invention may be seen to include a pair of molding trays 31A, 31B which are releasably connectable by a hinge mechanism 32 and used for fabricating and holding dental models made according to the present invention. As shown in FIG. 16 and as will be described in detail below, hinge mechanism 32 enables trays 31A, 31B to be pivoted between a mutually co-planar horizontally disposition as shown in FIG. 2, to a configuration in which one of the molding trays overlies the other in a generally parallel disposition, as shown in FIGS. 2 and 16.

As will be made clear in the ensuing description, only one of molding trays 31A, 31B need by provided with certain novel structural features according to the present invention, if a removable dental model cast is to be made of teeth in a single jaw of a patient. However, according to a preferred method of practicing the invention, trays 31A and 31B may be identical, and for the sake of brevity in the ensuing description, the letter suffix A or B is deleted unless necessary to distinguish between two trays, e.g., a tray in which a master dental cast is molded versus a tray in which an opposing cast is molded.

As shown in FIGS. 1–3, each tray 31 has a longitudinally elongated rectangular plan view shape. Tray 31 preferably has flat and parallel upper and lower surfaces 33, 34, respectively. Also, tray 31 has longitudinally elongated, rectangularly shaped, vertically disposed front and rear side walls 35, 36, a rectangularly shaped inner (hinge side), vertical end wall 37 and an outer vertically disposed end wall 38.

As shown in FIG. 1, tray 31 includes a thin rectangularly-shaped base plate or wall 42 which is located within the tray, disposed parallel to and between upper and lower surfaces 33, 34 of the tray. Base plate 42 forms with adjacent vertical inner walls of tray 31 in an upper part thereof of a relatively shallow rectangularly-shaped upper depression or upper trough 39, and in a lower portion thereof a similarly shaped lower trough 63. Trough 39 is concentric with the outer vertically disposed perimeter wall surface 40 of tray 31, and is nearly as large as the outer perimeter of the tray. Thus arranged, a thin rectangularly-shaped peripheral ring 41 is formed between trough 39 and outer vertical perimeter wall surface 40 of tray 31. Peripheral ring 41 around trough 39 has a flat, horizontally disposed base wall 42. Peripheral ring 41 has disposed perpendicularly upwards from the base wall 42 an inner peripheral wall 43 which has inner wall surfaces, including front longitudinally disposed inner surface 45, rear longitudinally disposed inner surface 46, and shorter transverse end surfaces, i.e., left transverse inner surface 47, and right transverse inner surface 48.

As shown in FIG. 1, larger front and rear inner wall surfaces 45, 46 of peripheral ring 41 have formed therein a plurality of ribs 49 which protrude inwardly towards a longitudinal center line of trough 39. Ribs 49 protrude vertically upwardly of base wall 42, and form between each adjacent pair of ribs a vertically disposed notch or groove 50. As will be described in detail below, alternating ribs and grooves 49, 50 form complementary grooves and ribs in outer vertical surfaces of the base of a dental model cast formed in trough 39 by solidified liquid die stone poured into the trough, thus enabling the bases and individual segments cut from the base, to be removably returned to exact pre-existing locations within tray 31, because of the indexing action of the ribs and grooves being insertably received within complementary-shaped grooves and ribs molded into the sides of the model cast by hardened liquid die stone. As shown in FIG. 3, lower portions of front and rear wall surfaces 45, 46 adjacent to lower trough 63 are optionally provided with ribs and grooves 49B, 50B which may be extensions of ribs and grooves 49, 50.

Referring now to FIGS. 1, 2, and 3, it may be seen that tray 31 is provided with front and back or rear abutment flanges 55F, 55B, which protrude outwardly from front and rear walls 35, 36, respectively, of tray 31. As shown in the figures, each abutment flange 55F, 55B has the shape of a horizontally disposed, thin, longitudinally elongated rectangular rib or web which has an outer vertical wall surface 56 that is spaced outwards from an outer front or rear wall of tray 31, and flat and parallel, horizontally disposed, upper and lower surfaces 57, 58, respectively. The function of front and rear abutment flanges 55F, 55B are described below.

Referring now to FIGS. 1 and 3, it may be seen that base wall 42 of trough 39 in molding tray 31 has a flat upper surface 59, and includes an outer rectangular ring-shaped portion 60 which is joined to the inner wall surfaces of the front, rear, inner and outer end walls of the tray. Base wall 42 also includes a concentrically located, longitudinally elongated rectangularly-shaped center panel 61. Base wall 42 has a thickness of less than the height of tray 31, e.g., about 1/16 inch for a tray height of about 7/16 inch, and upper surface 59 of base wall 42 is located about 1/16 inch below upper peripheral edge wall 33 of the tray. Thus arranged, base wall 42 forms within a lower portion of tray 31 a relatively deep, e.g., about 3/8 inch, lower upwardly concave opening or "matrix" trough 63 which protrudes upwardly from lower peripheral face 64 of the tray.

Figure 23:
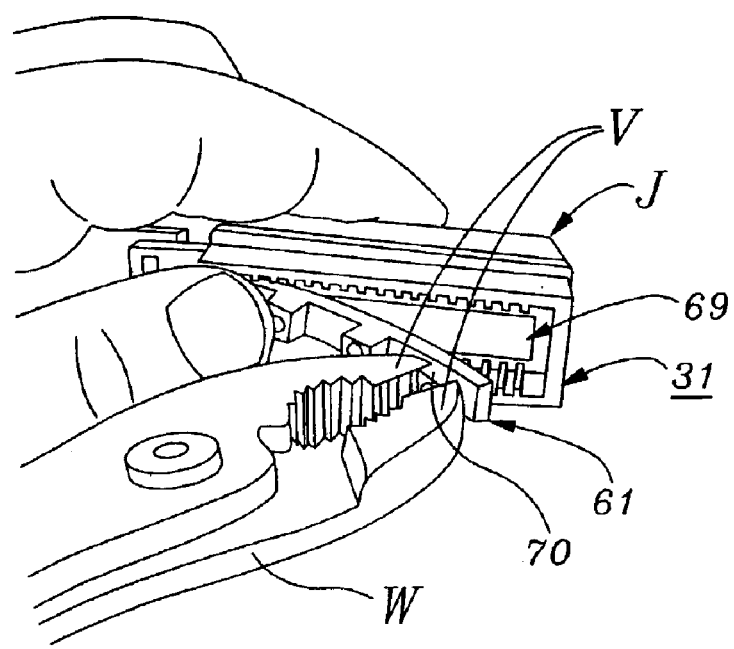
FIG. 23 is a perspective view of an alternative method for removing a frangible base plate from a tray comprising a component of the apparatus according to the present invention, without simultaneous ejection of a dental model cast from the tray, as shown in FIG. 12.

Referring still to FIGS. 1 and 3, it may be seen that center panel 61 of base wall 42 is connected to outer rectangular ring-shaped portion 60 of the base wall by a plurality of readily breakable, or frangible members 65. Thus, as shown in FIG. 3, outer vertical wall surface 66 of base wall center panel 61 is joined to inner vertical wall surface 67 of ring-shaped portion 60 of the base wall by a plurality of thin, breakable pins 65, e.g., a pair of front and rear pins and a pair of left and right pins. In a preferred embodiment, a tray 31 is fabricated as a unitary molded plastic part, with outer surface 66 of center panel 61 angled downwardly and inwardly away from adjacent inner wall surface 67 of ring-shaped outer portion 60 of base wall 42. With this construction, pins 65 may be readily molded to have a thickness substantially less than that of center panel 61, thus enabling the pins to be readily broken and thereby permitting the center panel to be broken away and removed from tray 31. With center panel 61 thus removed from tray 31, base wall 42 of the tray has through its thickness dimension a concentrically located, longitudinally elongated rectangular-shaped aperture 69, as shown in FIG. 23.

As shown in FIG. 3, center panel 61 of tray base wall 42 preferably is provided with one or more bosses 70 which protrude perpendicularly downwards from the lower surface 71 of the base wall. Although the exact shape and size of bosses 70 is not critical, the embodiment of tray 31 shown in FIG. 3 has three square cross-section bosses 70 which each have a flat lower surface 72 and a blind circular bore 73 which extends perpendicularly upwards from the lower surface. The three bosses 70 include a longitudinally centrally located center boss 70C, and left (inner) and right (outer) bosses 70L, 70R spaced equal longitudinal distances away from the center boss. The function and purpose of bosses 70 is described below.

Referring still to FIGS. 1, 2 and 3, it may be seen that each tray 31 has protruding horizontally outwards from a short end wall 37 thereof a hinge coupler bracket 74 for releasable attachment to hinge mechanism 32. Each hinge coupler bracket 74 has a shape approximating that of an L-bracket, an upright leg of which is bifurcated into two spaced apart, parallel plates. Thus, as shown in FIGS. 1–3, hinge coupler bracket 74 includes a rectangularly-shaped base plate 75 which protrudes outwardly from end wall 37 of tray 31. Base plate 75 has horizontally disposed upper and lower surfaces 76, 77 which are parallel to upper surface 33 of tray 31. Upper surface 76 of bracket base plate 75 is preferably recessed below upper surface 33 of the perimeter edge wall of tray 31, and has protruding perpendicularly upwards therefrom a first, outer rectangularly-shaped upright leg plate 78. Outer upright leg plate 78 has an outer vertical surface 79 which is co-planar with outer vertical edge wall 80 of a base plate 75.

Bracket 74 includes a second, inner upright leg plate 81 which is shaped similarly to outer leg plate 78, and which protrudes perpendicularly upwards from base plate 75 at a location spaced longitudinally inwardly from the outer upright leg plate. Inner upright leg plate 81 has an outer vertical wall surface 82 which is spaced longitudinally inwards of and parallel to an inner vertical wall surface 83 of outer leg plate 78. Preferably, a rectangularly-shaped aperture 84 is formed through base plate 75 of bracket 74, between outer and inner upright leg plates 78, 81. The purpose of aperture 84 is to facilitate elastic flexure of the outer and inner leg plates away from and towards one another, thereby facilitating elastic gripping engagement of hinge mechanism 32, as will be described below.

Referring still to FIGS. 2, 3A, 3B, 6, and 7, it may be seen that hinge mechanism 32 of apparatus 30 includes a pair of rectangular plan-view hinge members 85, 86, each having a thin upper rectangularly-shaped plate 87,88, respectively. Plate 87 has a pair of spaced apart, coaxially tubular extensions 89,90, which protrude upwardly from an inner end of the plate, parallel thereto. Plate 88 has a single, centrally located tubular extension 91 which fits coaxially between tubular extensions 89, 90 of plate 87, and is hingedly joined thereto by an elongated cylindrical hinge pin 91A which is disposed rotatably through bores (not shown) of the tubular extensions. The other parts of hinge members 85, 86 are identical, and include a larger rectangularly-shaped coupler plate 92 which depends perpendicularly downwardly from outer edge 93 of each upper plate. Coupler plate 92 has at opposite sides of a lower horizontal edge wall 94 thereof a pair of vertically disposed, L-shaped guide members 95 which form therebetween a pair of vertically disposed C-shaped channels 95A which are adapted to vertically upwardly insertably receive an inner upright leg plate 81 of a tray 31.

Figure 3A:
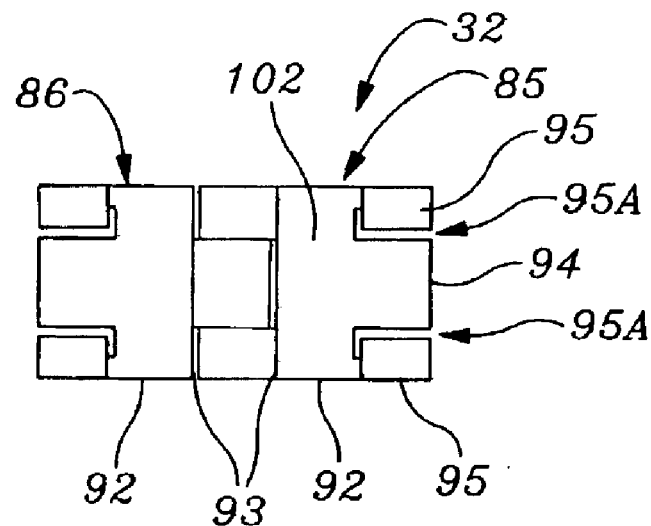
FIG. 3A is an upper plan view of the hinge coupler of FIG. 3.
Figure 3B:
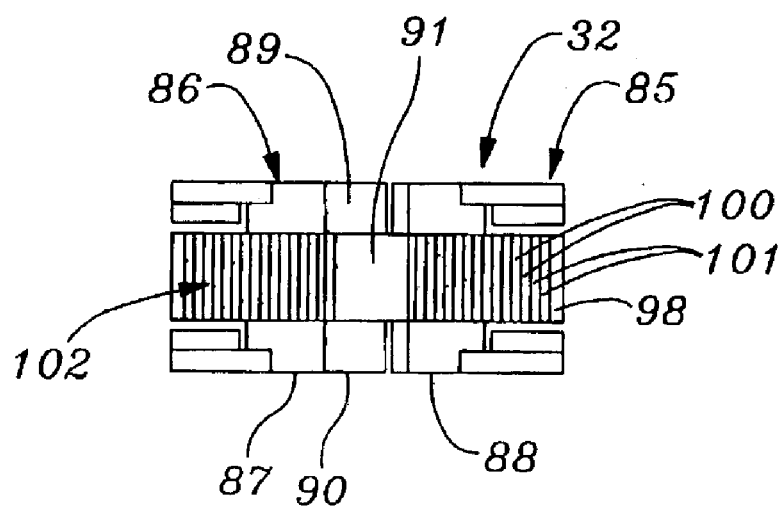
FIG. 3B is a lower plan view of the hinge coupler of FIG. 3.

Each hinge member 85, 86 also has protruding laterally inwardly from the L-shaped guide member 95 a vertically disposed lug member 96. Each lug member 96 has an inner vertical edge wall 97 which is located parallel to and laterally spaced apart from an inner vertical edge will 98 of coupler plate 92. As shown in FIG. 2, inner facing edge walls 97 of lug members 96 abut to limit inward pivotable motion of the coupler plates to a parallel position. As shown in FIG. 3B, inner vertical edge wall 98 of each coupler plate 91 preferably has formed therein a plurality of parallel, horizontally disposed, triangular cross-section ribs 100 which alternate with grooves 101 to form a washboard-like surface 102. The thickness of hinge coupler plate 92, measured between the vertices of triangular webs 100 and outer surface 102 of the coupler plate, is slightly greater than the spacing between an inner and outer faces 83, 82 of outer and inner leg plate uprights 78, 81 of hinge coupler bracket 74 of tray 31. Thus, when coupler plate 92 is inverted downwardly into the space 104 between the tray upright leg plates, the latter flex elastically slightly apart, and ribs 100 bite into the plates slightly, thus frictionally engaging the coupler plate with the tray legs. A description of certain components of a pin tray dental prostheses modeling system according to the present invention having been given, the manner of using those components according to methods of the present invention is presented below.

Figure 4:
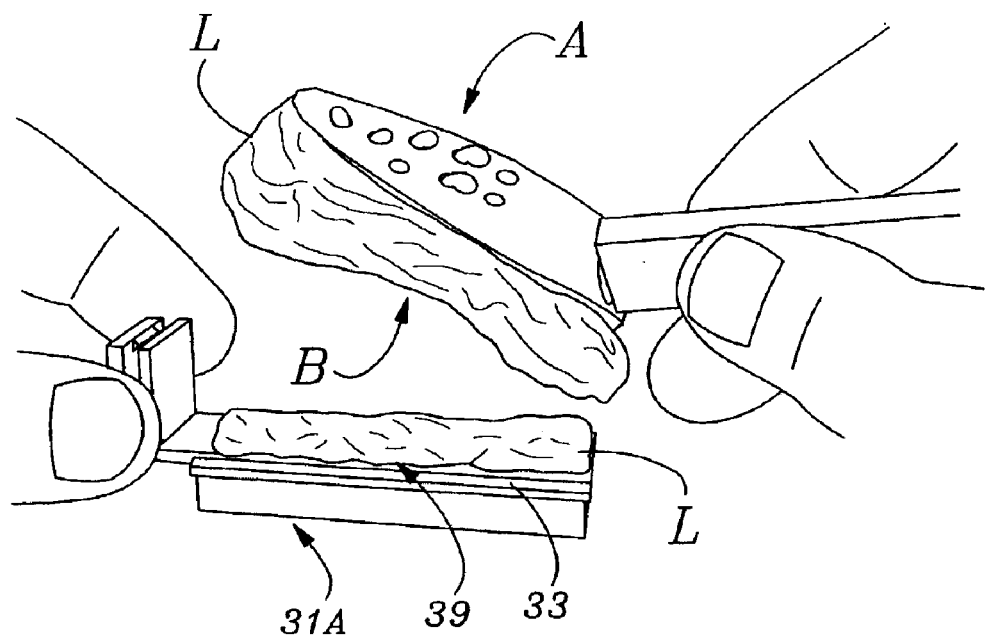
FIG. 4 is a perspective view showing a first step of a method for making a modeling cast or "arch" from a single quadrant impression mold made of a group of a patient's teeth located in either an upper or lower jaw and including one or more teeth to be renovated.
Figure 5:
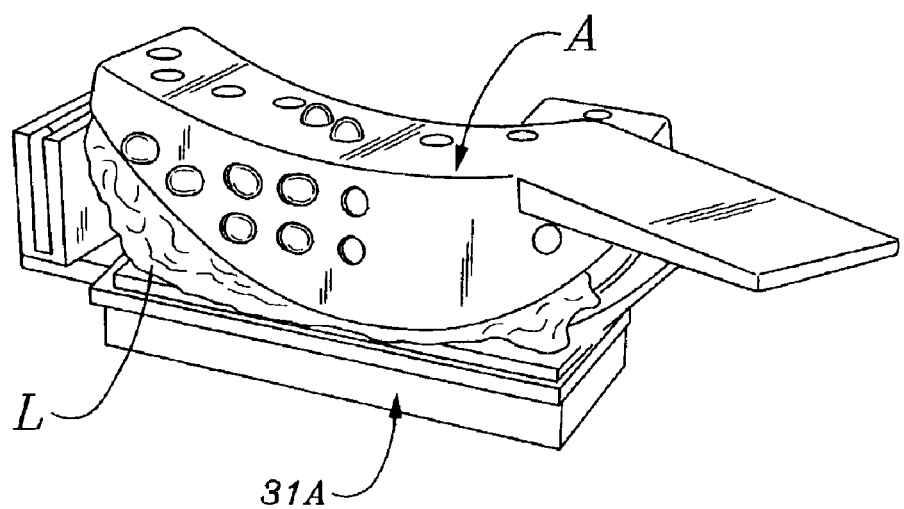
FIG. 5 is a perspective view of the arrangement of FIG. 4 showing a second step in making a dental model cast from a single quadrant impression.

FIG. 4 illustrates a first step in making a dental prostheses model cast or "arch" from a single quadrant impression mold made of a group of a patient's teeth located in an upper or lower jaw of the patient. As shown in FIG. 4, the trough 39 in the upper portion of a first molding tray 31A is fitted with a semi-liquid die stone material such as plaster of Paris, to a level slightly above upper peripheral wall 33 of the tray. As is also shown in FIG. 4, a dental impression mold A containing imprints B of a patient's teeth is also filled to overflowing with liquid die stone. The filled impression A is then inverted, positioned over tray 31A, and pressed down onto the semi-liquid die stone in the tray, as shown in FIG. 5. The semi-liquid die stone in impression A thus co-mingles with that in tray 31A. Time is then allowed for the liquid die stone in tray 31A to harden into a stone-like cast. Next, impression mold A is peeled upwardly and off from the hardened die stone in tray 31, leaving therein a cast C which is an accurate replica of teeth which impressed or imprinted the impression mold, as shown in FIG. 6.

Figure 8:
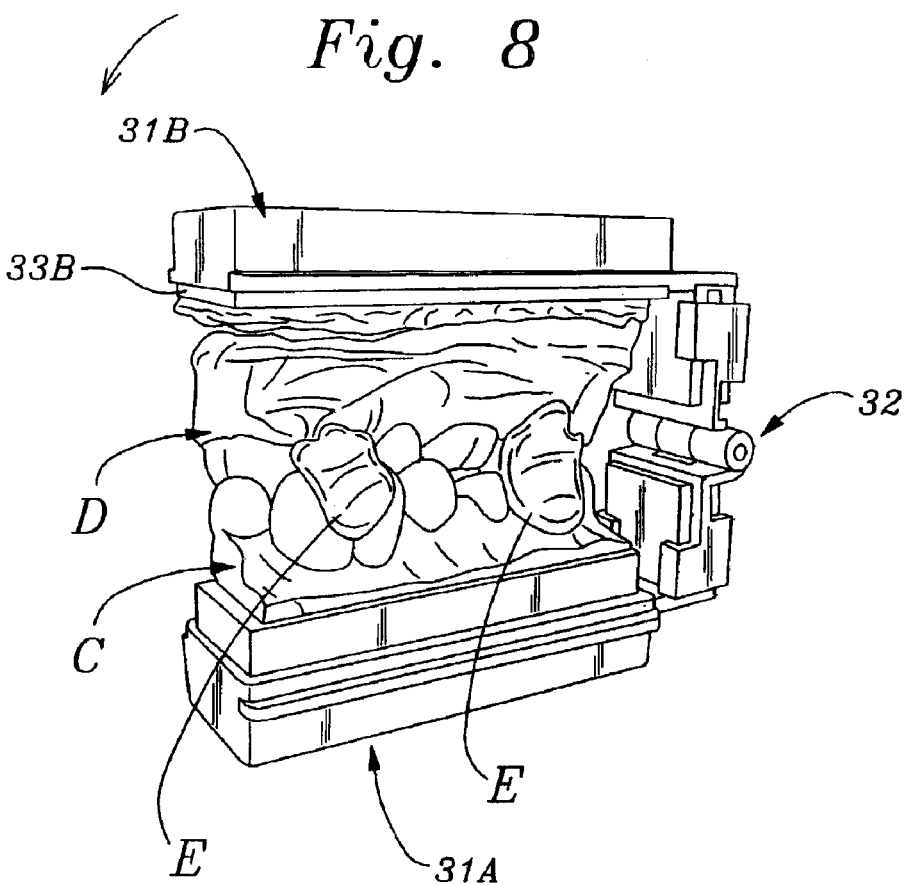
FIG. 8 is a view similar to that of FIG. 7, but showing the opposing tray pivoted on the axis of the hinge coupler to thereby bring the semi-liquid die stone material in the opposing tray and the upper surface of the opposing casting into contact to thereby co-mingle and cohere upon hardening, thus securing the opposing cast to the opposing tray.

Then, as shown in FIG. 6, a cast D made of an impression taken of teeth opposing those which are to be restored and which imprinted impression A is positioned above first, master cast C, which replicates teeth for which prostheses are to be fabricated. Opposing cast D is positioned in proper occlusal contact with master cast C, and temporarily secured in that configuration by blobs of wax E, for example, as shown in FIG. 6. Next, as shown in FIG. 7, a second, opposed tray 31-B, coupled by hinge mechanism 32 to tray 31-A containing master dental model cast C, is filled to overflowing with liquid die stone L, as is upper surface of opposing cast D. Then, as shown in FIG. 8, the upper surface 33B of opposing tray 31-B is pivoted towards contact with upper surface F of opposing cast D, causing die stone in the upper impression to co-mingle with that in the opposing tray. Time is once again allowed for the liquid die stone in opposing tray 31-B and opposing cast D to harden. Wax blobs E are then heated slightly to melt the wax, enabling opposing tray 31-B, now secured to opposing cast D by solidified die stone, to be pivoted away from master cast C. Further processing steps used to complete pinned dental model cast C are described below, following a description of preliminary steps for making master and opposing casts from a double-bite, or triple tray impression; the final steps of making finished casts are the same for both single quadrant and triple tray impression casts.

FIGS. 9–11 illustrate a method of making dental model casts from double-bite or triple-tray impressions according to the present invention.

FIG. 9 shows a first step in making a dental prostheses model cast from a double-bite or triple-tray impression mold G made from a patient's teeth located in lower or upper jaw and including teeth which are to be replaced by or fitted with one or more prosthetic restorations or replacements, and occluding teeth in an opposing jaw. As shown in FIG. 9, trough 39 in the upper portion of a first molding tray 31-α is filled with a semi-liquid, hardenable modeling substance such as plaster of Paris or die stone, to a level slightly above upper peripheral wall surface 33 of the tray. As is also shown in FIG. 9, a concave depression in a first, master side H of two-sided dental impression G imprinted with teeth which are to be restored, is also filled to overflowing with liquid die stone. The filled master side impression H is then inverted, positioned over tray 31-α, and pressed down into the semi-liquid die stone in the tray, as shown in FIG. 10. The semi-liquid die stone in the impression H thus co-mingles with semi-liquid die stone material in tray 31-α. Time is then allowed for the liquid die stone in tray 31-α and master impression H to harden into a stone-like master cast J. Next, liquid die stone L is poured to overflowing into a second, opposing tray 31-β, which is pivotably connected to first tray 31-α by a hinge mechanism 32. As is also shown in FIG. 11, a concave depression in second, opposing side K of two-sided impression mold G imprinted with teeth in a jaw opposed to the jaw containing teeth to be restored, is filled to overflowing with liquid die stone L. As shown in FIG. 11, opposing tray 31-β is then pivoted towards contact with the upper surface of semi-liquid die stone in concave impression area K of the opposing impression, causing die stone in the upper, opposing impression to co-mingle with die stone in the upper, opposing tray. Time is once again allowed for the semi-liquid die stone in opposing tray 31-β and opposing impression K to harden into a stone-like opposing cast L. Next, a master dental model cast J formed in master tray 31-α is temporarily and replaceably removed from the tray, in the following manner.

A preferred method for removing master dental model cast J from tray 31-α consists essentially of exerting an upwardly directed force on center panel 61 of base wall 42 of the tray which is of sufficient strength to break pins 65 which join the center panel to peripheral ring panel 60 of the base wall, and then pushing upwardly on that portion of the lower surface M of a cast J that is accessible through aperture 69 through the base wall. According to a preferred method of removing cast J from tray 31-α, a template 190 and tool 191, shown in FIGS. 19 20A and 20B, are employed.

Figure 12:
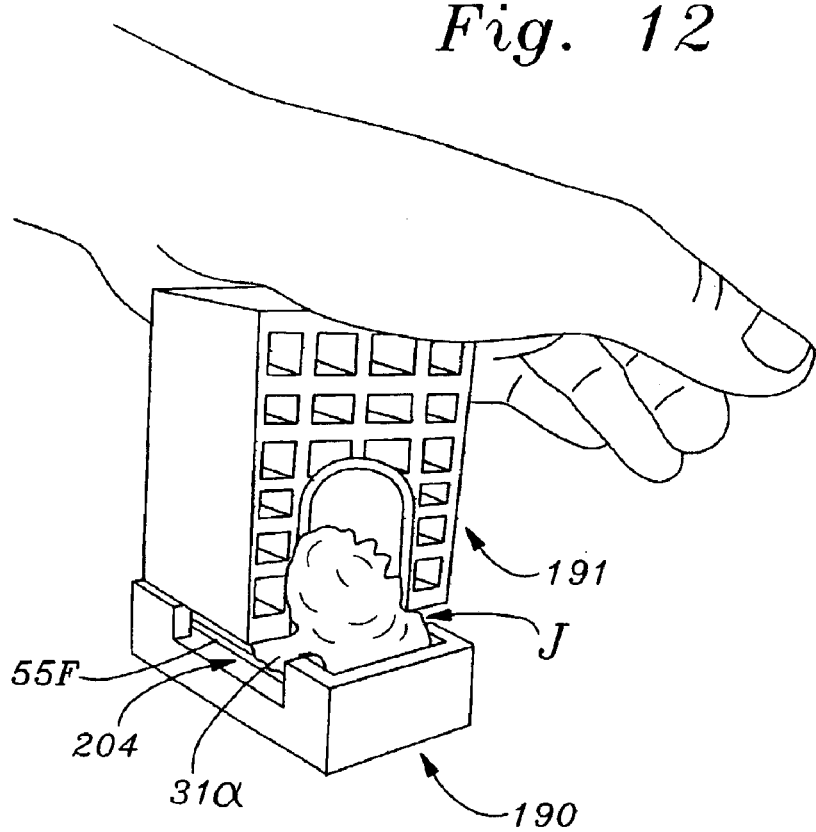
FIG. 12 is a perspective view of a fourth step of the double-tray method of FIG. 10, as well as that the single tray method of FIGS. 4–8.

As shown in FIG. 19, template 190 includes a flat base 192 having a longitudinally elongated, rectangular shape. Base 192 of template 190 has protruding perpendicularly upwards from a flat upper surface 193 thereof a longitudinally elongated, rectangularly shaped lug 194 which has a vertically disposed peripheral wall surface 195 that is located concentrically with respect to the outer peripheral wall surface 196 of the base, and has a flat upper surface 197 disposed parallel to upper surface 193 of base 192. Template 190 also includes at opposite short ends 198, 199 thereof a pair of opposed, vertically disposed guide structures 200, 201 which have formed therein a pair of opposed inner facing C-shaped guide spaces 202, 203 which together form an open rectangular-shaped tray receipt space 204 which is concentric with outer peripheral wall surface 195 of lug 194. As shown in FIGS. 12 and 19, tray receipt space 204 has a rectangular plan view shape which is similar to that of tray 31, but of larger size so that the tray may be loosely inserted downwardly into the space, the bottom surfaces 72 of bosses 70 of base wall 41 abutting upper surface 197 of lug 194.

As shown in FIGS. 20A and 20B, a knock-out tool 191 according to the present invention includes a rectangular block-shaped body 205 which has vertically elongated, rectangularly-shaped parallel left and right side walls 206L, 206R and vertically elongated, rectangularly-shaped parallel front and back side walls 207F, 207B, which are perpendicular to the side walls. Body 205 has disposed perpendicularly through left and right side walls 206L, 206R thereof an arch-shaped tunnel 208. Body 205 of tool 191 has a flat, horizontally disposed upper end wall 209, and a flat lower wall surface 210. Tunnel 208 penetrates lower wall surface 210, thus defining between front and back side walls 207F, 207B a pair of front and rear legs 211F, 211B which have opposed lower, inner vertical wall surfaces 212F, 212B which border the tunnel. Legs 211F, 211B each has at a lower end thereof a laterally disposed rectangularly shaped foot flange 213F. 213B which has a flat lower surface coextensive with lower wall surface 210 of body 205, and flat, parallel upper surfaces 214F, 214B. Foot flanges 213F, 213B protrude horizontally a short distance inwards into tunnel 208, and have vertically disposed, inner facing parallel end walls 215F, 215B. Foot flange front and back end walls 215F, 215B are spaced apart at a distance slightly greater than the space between the outer surface of front and peripheral upper edge walls of tray 31.

FIG. 12 illustrates the use of template 190 and knock-out tool 191 to remove a dental cast J from tray 31-α. As shown in FIG. 12, tray 31-α containing cast J is placed in opening 204 of template 190, with bottom surfaces 72 of bosses 70 supported on upper surface 197 of lug 194. Knock-out tool 191 is then positioned above front and back abutment flanges 55F, 55B of tray 31 with lower surfaces of front and back knock-out tool flanges 213F, 213B contacting the upper surfaces of the abutment flanges of the tray. A sharp blow is then delivered downwardly to the upper surface of the knock-out tool which causes the knock-out tool flanges to exert a downward force on the tray abutment flanges, thus causing lug 197 to be pushed upwardly on center panel 61 of tray base wall 42, breaking pins 65 which join the center panel to rectangular ring-shaped portion 60 of the base wall, and thereby ejecting cast J upwardly and out from the tray.

Figure 13:
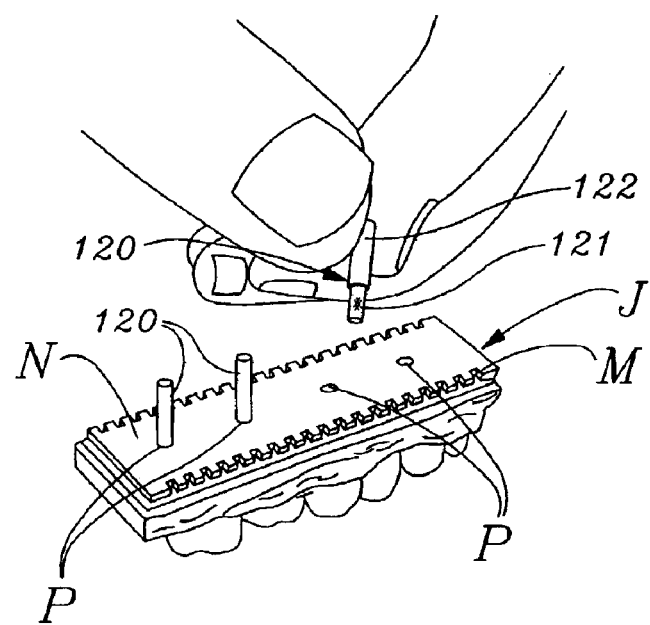
FIG. 13 is a perspective view of a fifth step in the double tray method of FIG. 10, as well as the single tray method of FIGS. 4–8.

As shown in FIG. 13, a fifth step in making a dental prostheses model according to the present invention consists of drilling blind pin bores P into the base M of an inverted cast J, at locations aligned with portions of the cast which are to be severed from adjacent portions of the cast, to thereby form die segments which are to be used as models for dental prostheses. Pin bores P are also drilled into locations of the base corresponding to portions of the cast adjacent to die segments.

After pin bores P have been drilled into cast J as described above, cylindrical metal pins 120 are inserted into the base. As shown in FIG. 13, each pin has a short knurled end 121 and a longer smooth shank 122. Pin bores P are drilled to a depth approximating the length of knurled end 121 of pin 120, so that the smooth shank 122 protrudes perpendicularly downwards from lower face N of cast J. Pins 120 are preferably secured in pin bores P by coating knurled ends 121 of each pin with adhesive before inserting a pin into a bore.

Figure 14:
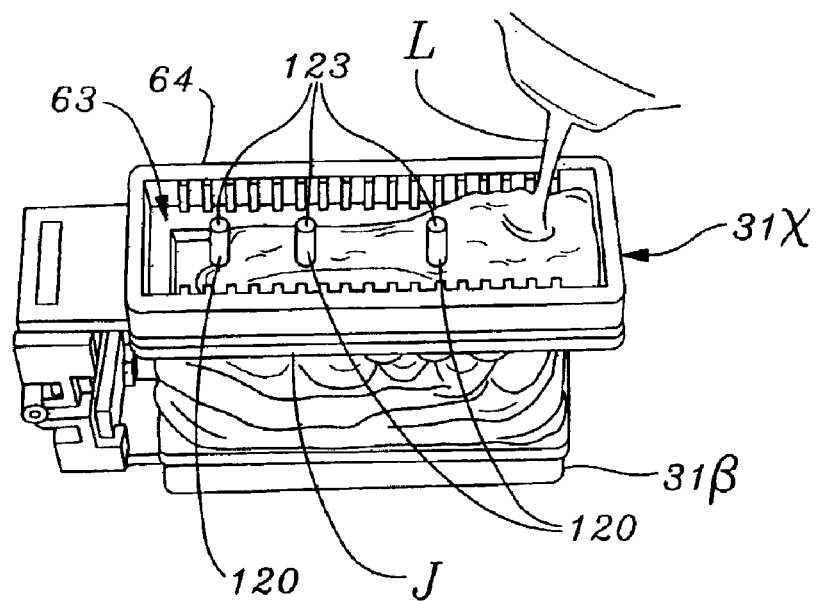
FIG. 14 is a perspective view of a sixth step in the double tray method of FIG. 10, as well as the single tray method of FIGS. 4–8.
Figure 15:
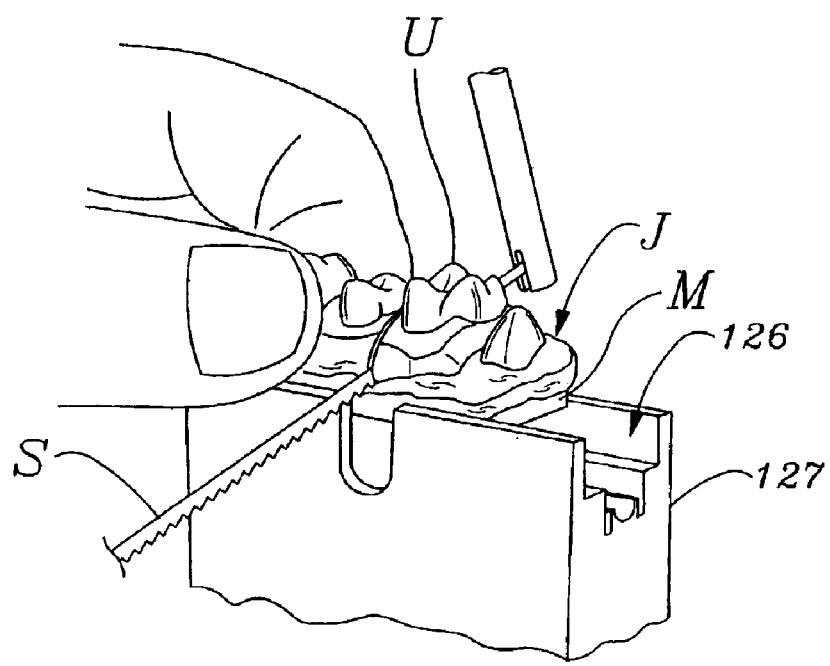
FIG. 15 is a perspective view of a seventh step in the double tray method of FIG. 10, as well as the single tray method of FIGS. 4–8.

FIG. 14 illustrates a fifth step in making a dental prostheses model according to the present invention. As shown in FIG. 14, a release agent is applied to the outer surfaces of pins 120, cast J is re-inserted into trough 39 of tray 31 and the tray is inverted. A release agent is applied to lower face N of cast J, and liquid die stone L is then poured into open lower portion 63 of the tray, to a level between the lower end faces 123 of the pins, and the lower peripheral rim 64 of the tray. Liquid die stone within the lower portion is allowed to harden to form a rectangular block-shaped, "stone matrix" 125, as shown in FIGS. 16 and 18. Cast J is once again withdrawn from trough 39 of tray 31, a task which is facilitated by exerting pressure on lower faces 123 of pins 120. Then, as shown in FIG. 15, base M of pinned cast L is placed upright in a horizontal channel 126 formed in the upper surface of a sawing stand fixture 127 of the type shown in FIG. 21. A saw S is then used to make vertical cuts T through cast J, on each side of a portion of the cast which is to be used as die segment U for use as a dental prostheses model. After one or more die segments U have been severed from dental model cast J, the die segments and adjacent portions of the cast may be repeatedly re-installed in tray 31 at precisely indexed locations, owing to the interlocking action of ribs and grooves of the cast engaging complementary grooves and ribs in the inner side walls of tray 31. FIGS. 16, 17, and 18 show a completed articulateable model of a master cast J with replaceable die segments, and an opposing cast fabricated by the above described apparatus and method according to the present invention.

FIGS. 23–27 illustrate a modification of the apparatus and method of the present invention described above. The modified apparatus and method employ the first three steps described above for both single quadrant and double-bite impression models. However, as shown in FIG. 23, a fourth step in the modified method comprises removing frangible center panel 61 of base wall 42 of tray 31 by grasping a center panel boss 70 between the jaws V of a pliers W, and exerting a pulling force sufficient to break center panel support pins 65. Blind pin bores P are then drilled into the base M of a cast J, in a manner described below, using a drilling alignment fixture 130 of the type shown in FIG. 22.

As shown in FIG. 22, drilling alignment fixture 130 includes an elongated, generally rectangular-shaped body 131 which has a flat lower surface 132, and a flat upper surface 133 in which is formed an elongated, shallow rectangular-shaped channel 134 which is adapted to receive a tray 31 containing therein the base M of a cast J.

Located in front and back sides of channel 134 are coplanar, horizontally disposed flat front and back ledges 135F, 135B which are of a proper spacing to support front and rear abutment flanges 55F and 55B of a tray 31.

Drilling alignment fixture 130 also includes a circular drill guide bushing 136 fitted through a lower wall 137 of the fixture. An index line 138 is inscribed on the outer surfaces of the fixture, in longitudinal alignment with the center line of a coaxial bushing 136.

Figure 24:
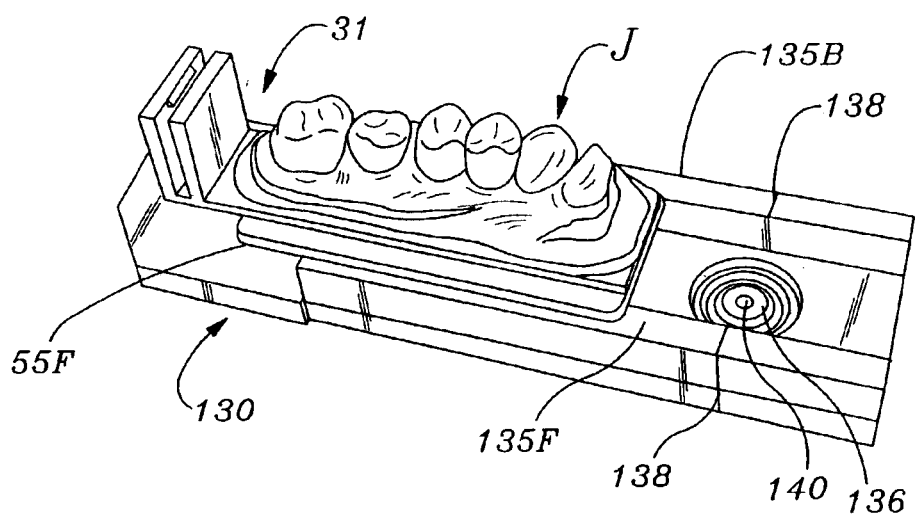
FIG. 24 is a perspective view showing the tray of FIG. 23, with the frangible base plate removed and slidably supported on the drilling alignment fixture of FIG. 22.
Figure 25:
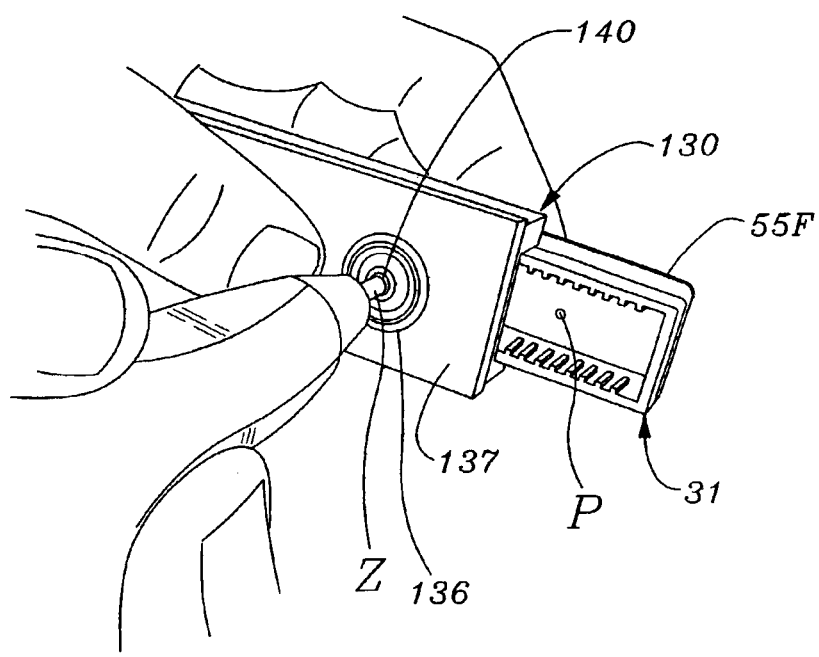
FIG. 25 is a perspective view showing how the drilling jig of FIGS. 22 and 24 is used to guide drilling of pin bores into the base of the dental model cast shown in FIGS. 23 and 24.
Figure 26:
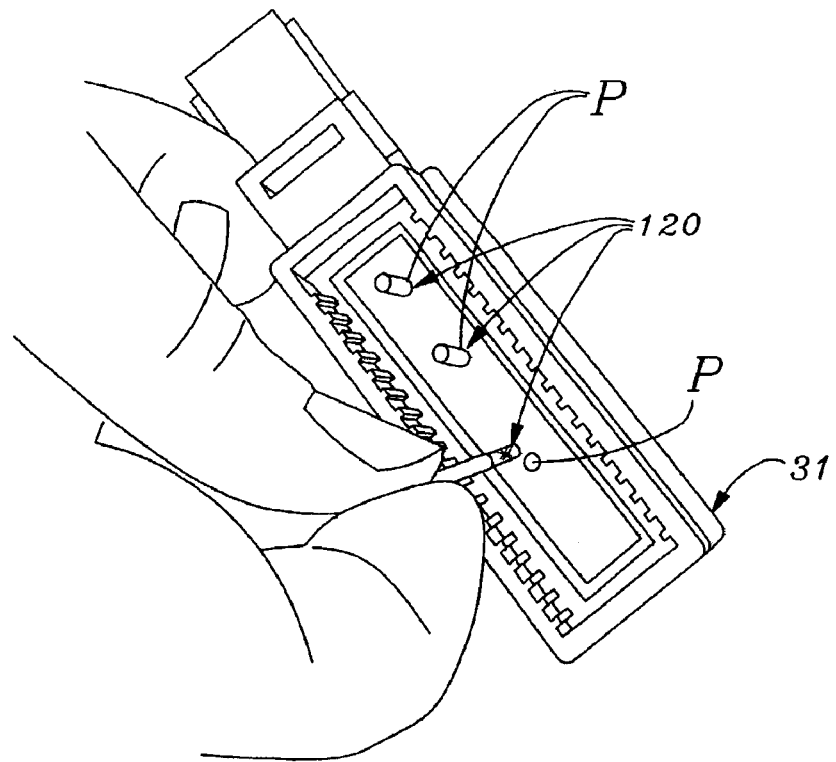
FIG. 26 illustrates one method for installing die segment pins in pin bores formed in the dental model cast as shown in FIG. 25.

As shown in FIGS. 24 and 25, drilling alignment fixture 130 is used by longitudinally sliding a cast J supported on ledges 135F, 135B of the fixture to thereby position a location of the cast where it is desired to insert a pin in longitudinal alignment with bushing bore index line 138. Drilling alignment fixture 130 and cast J are then rotated together as a unit to expose the lower surface 139 of the fixture, whereupon a drill bit is inserted through bore 140 of bushing 136, and rotated to drill a pin bore P at a desired location into the base M of cast J. Next, as shown in FIG. 26, pins 120 are inserted into and secured in pin bores P made as described above.

Figure 27:
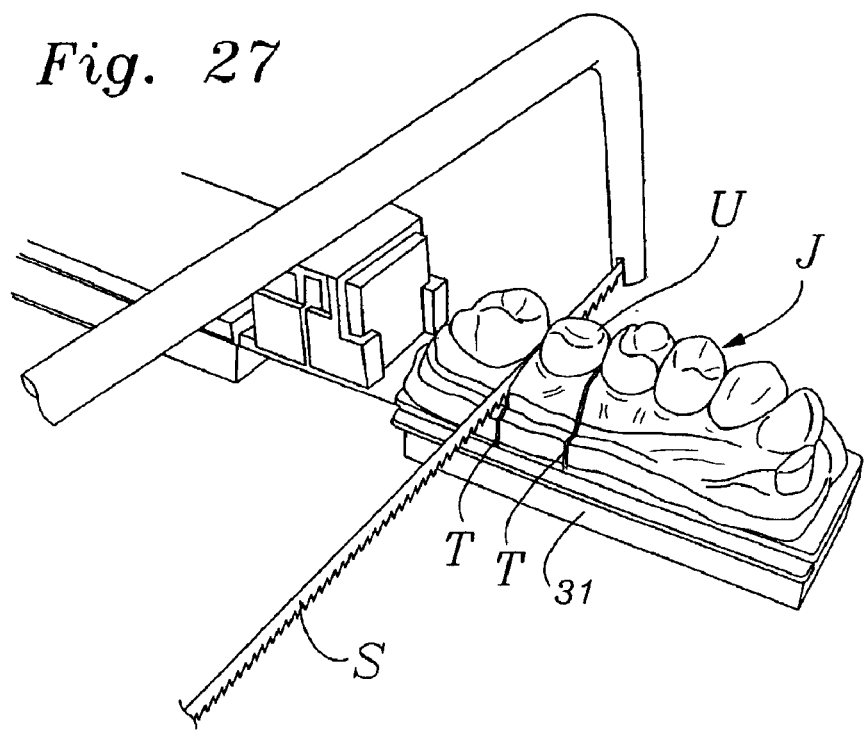
FIG. 27 illustrates one method for segmenting the dental model cast of FIGS. 23–26 into individual die segments.

A stone matrix 125 for receiving pins 120 is then molded in lower trough 63 of tray in the manner depicted in FIG. 14 and described above. Thus, as shown in FIG. 14, a release agent is applied to the outer surfaces of pins 120 and lower face N of cast J, and liquid die stone L is poured into lower trough 63, to a level between the lower end faces 123 of the pins, and the lower peripheral rim 64 of the tray. Time is then allowed for liquid die stone within lower trough 63 to harden into a rectangular block-shaped stone matrix 125, as shown in FIGS. 16 and 18. Then, tray 31 containing cast J, is re-oriented to an upright position, as shown in FIG. 27, and vertical saw cuts T are made into the cast to severe die segments from adjacent portions of the cast. Saw cuts T are made downwards just to the upper surface levels of front and back abutment flanges 55F, 55B. Cutting to the common level of the upper surface of the abutment flanges ensures that the saw cuts are made completely through the thickness of base M of cast J, thus enabling a pinned die segment U to be removed from tray 31, as shown in FIG. 18, and re-inserted into a precisely predetermined position relative to adjacent segments of the cast, which need not be removed, and repeatedly removed and re-inserted.

According to a first variation of the modified apparatus and method described above and illustrated in FIGS. 23–27, after pin bores P have been drilled into the base M of a cast J as shown in FIG. 25, the cast may be ejected from a tray 31, as for example, using a template 90 and knock-out tool as shown in FIG. 4. Then, pins 120 may be installed in the pin bores P of cast J in the manner indicated in FIG. 13, and the remaining steps of the basic embodiment of the method shown in FIGS. 13 through 15 and described above performed to produce a completed dental prostheses model. According to a second, slightly different variation of the modified apparatus and method depicted in FIGS. 23–27, pins 120 may be installed in bores P of cast J prior to ejecting the cast J from a tray 31, whereupon the steps of the basic embodiment depicted in FIGS. 14 and 18 and described above performed to produce a complete dental prostheses model.

Figure 28:
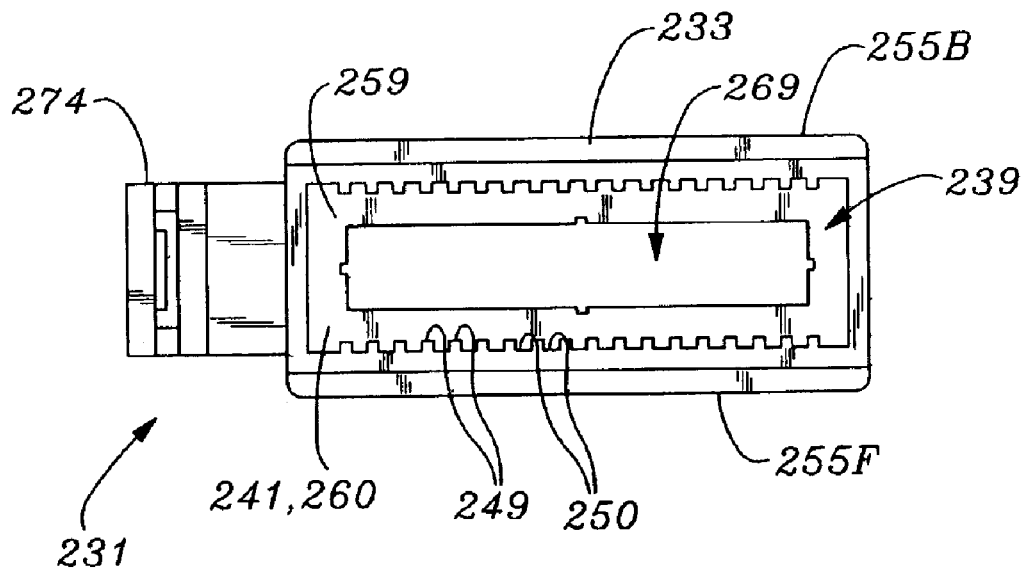
FIG. 28 is an upper plan view of a re-usable modeling tray for a pin tray dental prostheses modeling system according to the present invention.
Figure 29:
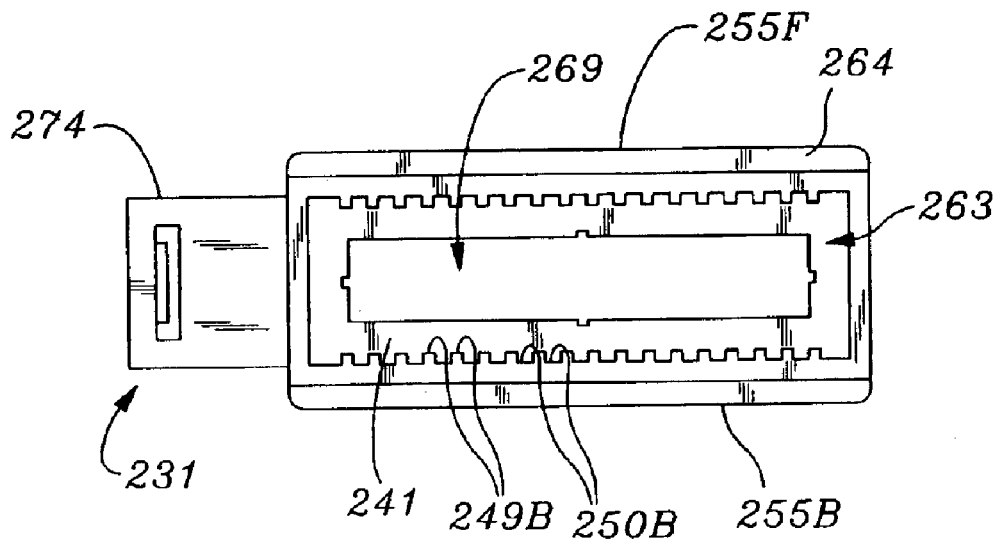
FIG. 29 is a lower plan view of the modeling tray of FIG. 28.

FIGS. 28 and 29 illustrate a re-usable modeling tray 231 for a pin-tray dental prostheses modeling system according to the present invention. Re-usable modeling tray 231 is substantially identical in structure and function to tray 31 described above, but does not have a center panel 61 or frangible support members 65 therefor. Instead, as shown in FIGS. 28 and 29, molding tray 231 has a base plate or wall 242 which consists of a rectangular ring-shaped peripheral portion 260 that circumscribes a concentrically located rectangular-shaped aperture 269. Thus constructed, tray 231 can be fabricated as an injection molded plastic part, or by modifying a new or used tray 31 by removing a center panel 61 from base wall 42 of the tray 31 by a method which will now be and described.

Figure 30:
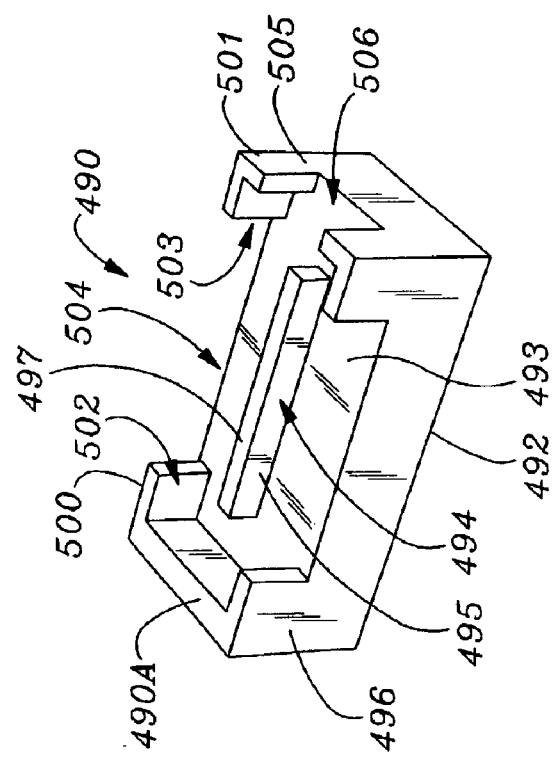
FIG. 30 is a perspective view of a template anvil for removing a die stone base matrix from a used molding tray according to the present invention.

Referring to FIGS. 30 and 31a template anvil 490 for use in removing a die stone matrix base from a used modeling tray 31 U according to the present invention may be seen to have a shape similar to that of template 90 described above. Thus, anvil 490 includes a flat base 492 which has a longitudinally elongated, rectangular plan view shape. Base 492 has protruding perpendicularly upwards from a flat upper surface 493 thereof a longitudinally elongated, rectangularly shaped lug 494 which has a vertically disposed outer peripheral wall surface 495 that is located concentrically with respect to the outer peripheral wall surface 496 of the base, and has a flat upper surface 497 disposed parallel to upper surface 493 of base. Upper surface 497 of lug 494 is recessed below the flat upper surface 490A of template anvil 490.

Template anvil 490 includes at opposed short transversely disposed left and right sides thereof a pair of opposed vertically disposed left and right guide structures 500, 501. Left and right guide structures 500, 501 have formed therein opposed inwardly facing openings 502, 503. Left and right openings 502, 503 have in plan view the shape of a C-shaped channel and its mirror image, respectively, which together form an open rectangularly-shaped tray receipt area 504 that is concentrically surrounds outer peripheral wall surface 495 of lug 494.

Figure 31:
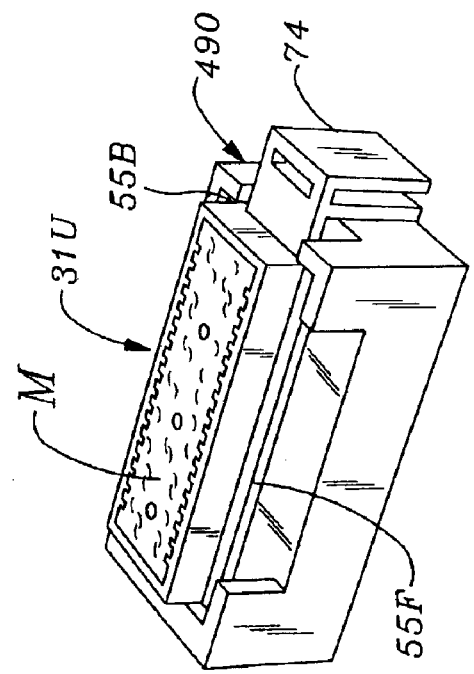
FIG. 31 is a perspective view showing a used molding tray placed on the template anvil of FIG. 30.

As shown in FIGS. 30 and 31, tray receipt space 504 of template anvil 490 has a rectangular plan view shape which is similar to that of tray 31, but of larger size so that the tray may be loosely inserted downwardly into the space. Referring still to FIGS. 30 and 31, it may be seen that right-hand wall 505 of right-hand guide structure 501 has formed therein a rectangular-shaped, vertically disposed slot 506 which extends downwardly from upper surface 490A of template anvil 490 to upper surface 493 of anvil 492. Slot 505 is provided to afford clearance for the hinge coupler bracket 74 of a tray 31, when the tray is inverted and placed in space 504 of the anvil. Thus, as shown in FIG. 31, a used tray 31U holding a dental model base matrix M is placed with the inverted upper surface of the base matrix seating on upper surface 497 of lug 494. As shown in FIG. 32, knock-out tool 91 is then positioned above front and back abutment flanges 55F, 55B of tray 31U, with lower surfaces of front and back knock-out tool flanges 113F, 113B contacting the upper surfaces of the tray abutment flanges. A sharp blow is then delivered downwardly to the upper surface of knock-out tool 91, causing the knock-out tool flanges to exert a downward force on the tray abutment flanges. This force in turn causes lug 497 to be forced upwardly on the inverted upper surface of base stone matrix M, thus ejecting the base stone matrix upwardly out of the bottom opening of the tray, as shown in FIG. 33. The ejected base stone matrix M is discarded, and used tray 31U may be substituted for a tray 231, which is used as follows.

Figure 34:
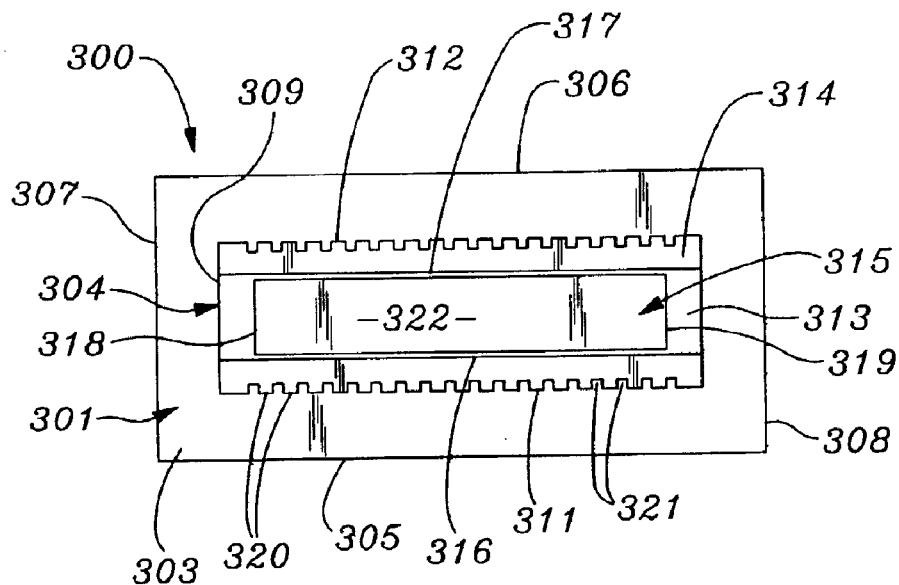
FIG. 34 is an upper plan view of a tray insert for use with the tray of FIGS. 28 and 29.
Figure 35:
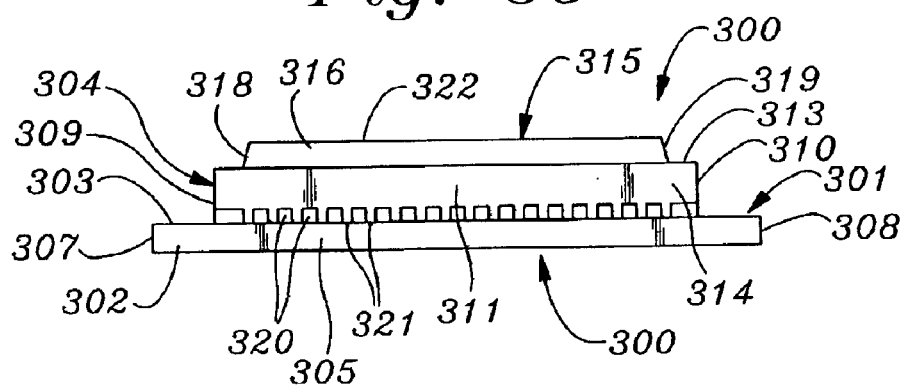
FIG. 35 is a front elevation view of the insert of FIG. 34, the rear elevation view being identical to the front elevation view.
Figure 36:
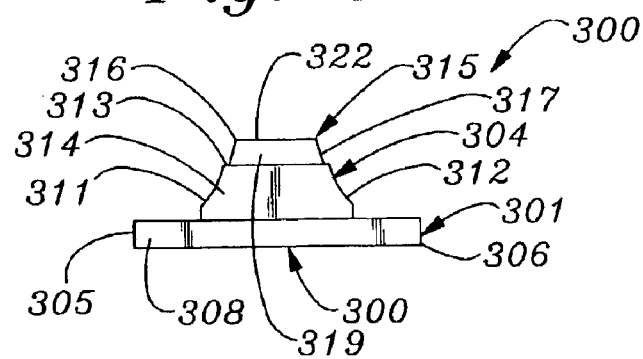
FIG. 36 is a right side elevation view of the insert of FIG. 35, the left side elevation view being identical to the right side elevation view.

FIGS. 34, 35, and 36 illustrate an insert 300 for use with modeling tray 231 according to the present invention. As shown in FIGS. 34, 35 and 36, insert 300 has a flat, longitudinally elongated, rectangular plan-view base plate 301. As shown in FIGS. 35 and 36, base plate 301 of insert 300 has a generally uniform thickness, and has flat and parallel lower and upper surfaces 302, 303, respectively. Referring to FIGS. 34, 35, and 36, insert 300 may be seen to include a longitudinally elongated, rectangular plan view boss 304 which protrudes upwards from upper surface 303 of insert base plate, the boss being concentrically located with respect to front, rear, left and right perimeter wall surfaces 305, 306, 307 and 308, respectively, of the base plate 301. As shown in FIGS. 34 and 35, boss 304 of insert 300 has generally vertically disposed left and right side walls 309, 310, and front and rear side walls 311, 312, which are inclined towards a vertical, longitudinally disposed mid plane of the boss. As shown in FIGS. 35 and 36, boss 304 has protruding upwardly from an upper surface 313 of a trapezoidally transverse cross section base 314 thereof a longitudinally elongated rectangularly-shaped lug 315.

Lug 315 has front and rear longitudinally elongated, generally vertically disposed edge walls 316, 317 which protrude upwardly from front and rear angled boss walls 311, 312, respectively, of boss 304. Also, lug 315 has generally vertically disposed left and right side walls 318, 319, which protrude upwardly from upper surface 313 of boss base 314, and has a flat upper surface 322 parallel to base plate 301 of the insert. As shown in FIGS. 34 and 35, left and right side walls 318, 319 of lug 315 are recessed short equal distances from left and right sides 309, 310, respectively of base 314 of boss 304.

Referring to FIGS. 34 and 35, it may be seen that front and rear side walls 311, 312 of boss 304 of insert 300 have formed in short, more generally vertically disposed lower portions thereof a plurality of alternating ribs 320 and grooves 321 which are adapted to mesh conformally with complementarily-shaped grooves 250B and ribs 249B, respectively, in lower trough 263 of tray 231.

Figure 37:
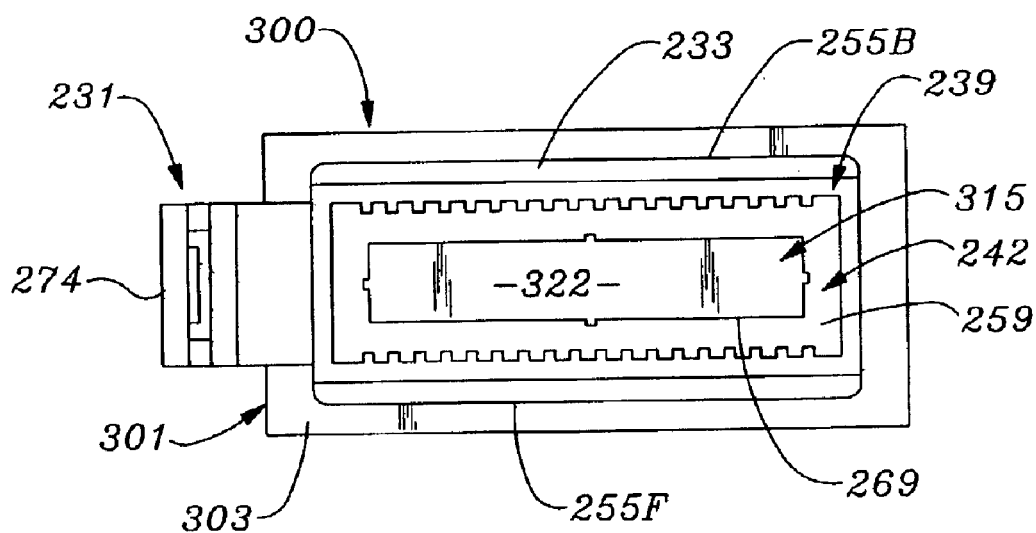
FIG. 37 is an upper plan view of the tray of FIG. 28, showing the insert of FIGS. 34–36 installed in the tray of FIGS. 28–29.
Figure 38:
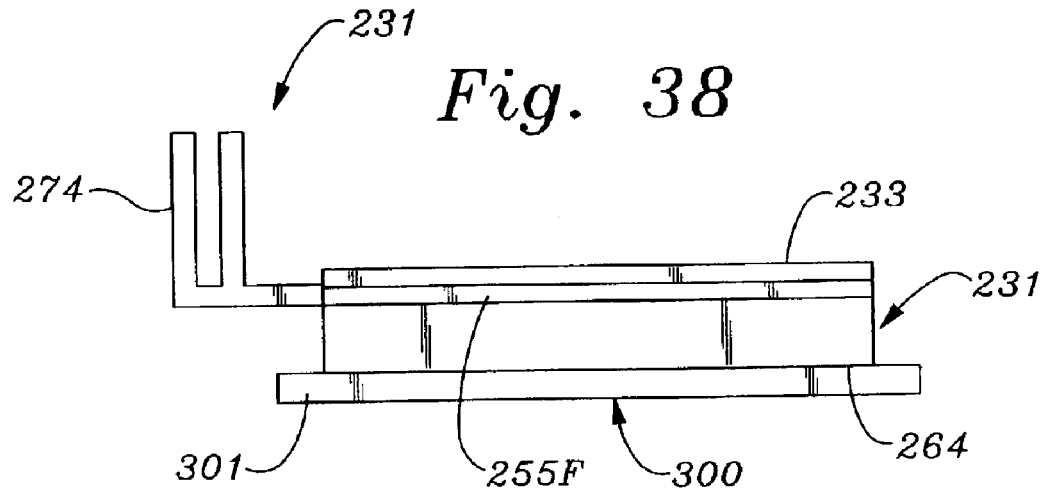
FIG. 38 is a front elevation view of the tray and installed insert of FIG. 37.

Referring now to FIGS. 37 and 38, it may be seen that insert 300, constructed as described above, is adapted to be fitted into lower trough 263 of tray 231, with lug 315 fitting conformally within aperture 269 through base wall 242 of the tray. Thus positioned, upper surface 322 of insert lug 315 is substantially flush with upper surface 259 of base wall 242 of tray 231.

Figure 39:
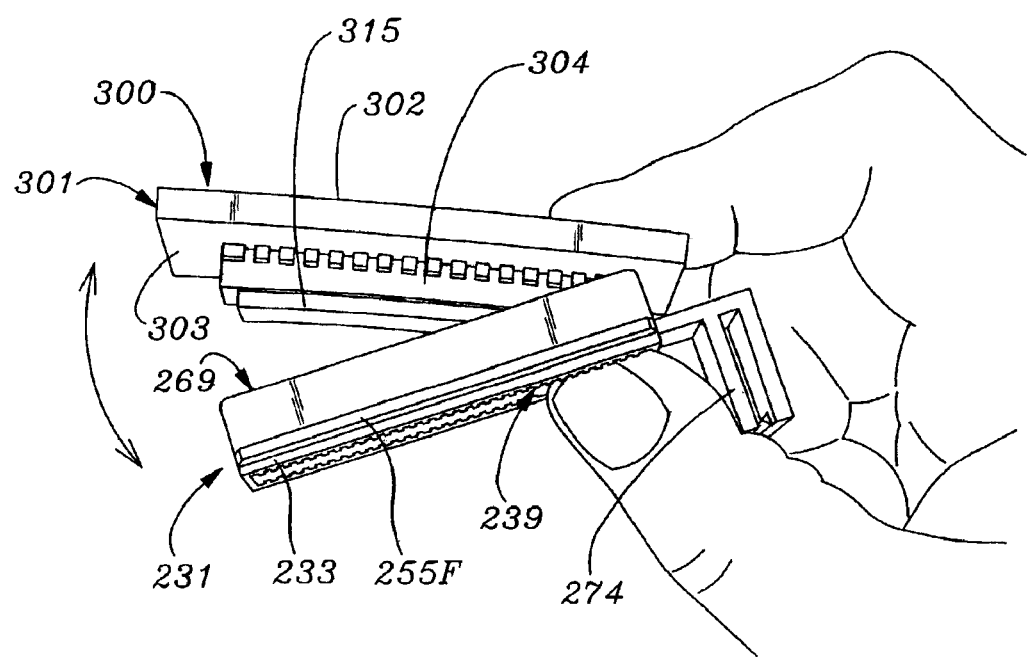
FIG. 39 is a front perspective view showing a method of removing the insert from the tray of FIG. 38.

In a preferred embodiment, tray insert 300 is made of a resilient material, e.g., an elastomeric polymer such as polyurethane. This choice of materials enables lug 315 to fit resiliently within aperture 269 through base wall 242 of tray 231 in a liquid tight seal therewith. Liquid die stone may then be poured into upper trough 239 of tray 231 to form the base of a dental model cast, in the manner shown in FIGS. 4 and 11 and described above. After liquid die stone has hardened to form a cast, insert 300 is readily withdrawn from lower trough 263 of tray 231, by grasping an edge of base plate 301 and exerting a downwardly directed parting force relative to the tray, as for example, by grasping an edge of the tray and an edge of the insert base plate between a thumb and forefinger and exerting a pinching force thereon, as shown in FIG. 39. Following removal of insert 300 from tray 231, a dental prostheses may be fabricated according to the steps shown in FIGS. 24–27 and described above, or according to the first or second variations described, which are also described above.

What is claimed is:

1. A molding tray for use in making a dental prostheses model from an impression mold having formed imprints of a patient's teeth, said molding tray comprising:

a. a hollow body having an upper surface, and a peripheral wall protruding downwardly from said upper surface to a lower surface, b. a base frame located within said body, said base frame having an upper surface located below said upper surface of said body and forming between said base frame, said upper surface and an inner surface of said peripheral wall of said body a shallow upper trough said base frame having an outer ring-shaped peripheral portion which circumscribes an aperture communicating with a hollow lower interior space within said body, c. a plurality of longitudinally spaced apart protuberances protruding inwardly from inner surfaces of opposed sides of said peripheral wall of said body, said protuberances alternating with grooves formed between said protuberances, d. an insert which has a lug portion that is adapted to be insertably received in said aperture in said base frame in a liquid-tight seal therewith, thus forming with said base frame a bottom wall for said upper trough, and e. whereby said insert may be inserted into said aperture in said base frame, liquid die stone is poured into said upper trough and hardened to comprise a base of a dental model cast, force exerted on said insert received in said base frame to remove said insert from said aperture in said base frame, pins installed in a lower surface of said cast base, said cast base returned to a predetermined index position within said tray enabled by engagement of said protuberances and spaces of said tray with complementary shaped spaces and protuberance molded into sides of said cast base, said cast and tray inverted, and liquid die stone poured into said hollow lower interior space of said tray to form upon hardening a base stone matrix for releasably receiving said pins protruding from said base of said cast.

2. The molding tray of claim 1 further including releasable attachment means for releasably attaching said tray to a second of said trays.

3. The molding tray of claim 2 wherein said releasable attachment means is further defined as comprising in combination a bracket protruding outwardly from a side wall of said body, and hinge mechanism means for pivotably coupling said bracket of said tray to a bracket of a second tray to thereby enable pivotable relative motion between said trays in a plane perpendicular to upper edge walls of said trays.

4. A re-usable molding tray for use in making a dental prostheses model from an impression mold having formed therein imprints of a patient's teeth, said molding tray comprising;

a. a hollow body having an upper surface, and a peripheral wall protruding downwardly from said upper surface to a lower surface, b. a base frame located within said body, said base frame having an upper surface located below said upper surface of said body and forming between said base frame, said upper surface and an inner surface of said peripheral wall a shallow upper trough, said base frame having an outer ring-shaped peripheral portion which circumscribes an aperture communicating with a hollow lower interior space within said body, c. a plurality of longitudinally spaced apart protuberances protruding inwardly from inner surfaces of opposed sides of said peripheral wall of said body, said protuberances alternating with grooves formed between said protuberances, d. an insert which has a lug portion that is adapted to be insertably received in said aperture in said base frame in a liquid-tight seal, thus forming with said base frame a bottom wall for said upper trough, e. whereby said insert may be inserted into said aperture in said base frame, liquid die stone is poured into said upper trough and hardened to comprise a base of a dental model cast, a force exerted on said insert received in said base frame to remove said insert from said aperture in said base frame, pins installed in a lower surface of said cast base, said cast base returned to a predetermined index position within said tray enabled by engagement of said protuberances and spaces of said tray with complementary shaped spaces and protuberance molded into sides of said cast base, said cast and tray inverted, and liquid die stone poured into said hollow lower interior space of said tray to form upon hardening a base stone matrix for releasably receiving said pins protruding from said base of said cast, and f. said base stone matrix being removable from said tray to thereby enable re-use of said tray to make another dental prostheses model.

5. The molding tray of claim 4 further including in combination ejection tool means for removing a die stone matrix base from said tray.

6. The molding tray of claim 5 wherein said ejection tool means is further described as including a template anvil which has a base and an upwardly protruding lug for supporting the upper surface of a base stone matrix in an inverted tray, and knock-out tool means for exerting downward force on said tray relative to said template anvil to thereby cause an upwardly directed reaction force to be exerted on said inverted upper surface of said stone matrix base sufficient to at least partially eject said matrix stone base from said tray.

7. The molding tray of claim 4 further including at least one pair of abutment flanges which protrude outwardly from an opposed pair of sides of said tray.

8. The molding tray of claim 7 further including in combination ejection tool means for removing a die stone matrix base from said tray.

9. The molding tray of claim 8 wherein said ejection tool means is further described as including a template anvil which has a base and an upwardly protruding lug for supporting the upper surface of a base stone matrix in an inverted tray, and knock-out tool means for exerting downward force on said tray relative to said template anvil to thereby cause an upwardly directed reaction force to be exerted on said inverted upper surface of said stone matrix base sufficient to at least partially eject said matrix stone bore from said tray.

10. The molding tray of claim 9 wherein said knock-out tool means is further described as including a block-shaped body which has an upper impacting surface adapted ro receive an impact force, and at a lower part of said body a pair of laterally protruding foot flanges which have lower surfaces adapted to press simultaneously against surfaces of said abutment flanges of said tray.

11. The molding tray of claim 4 wherein said aperture through said base frame is further defined as being formed by breaking from said outer ring-shaped peripheral portion thereof a center panel joined to said ring-shaped peripheral portion thereof by frangible members.

12. The molding tray of claim 11 further including at least one pair of abutment flanges which protrude from an opposed pair of sides of said tray.

13. A dental prostheses modeling apparatus including the molding tray of claim 12 and force applying means for applying a compressive force on said flanges relative to said center panel of said base frame sufficient to break said center panel away from said outer ring-shaped peripheral portion of said base frame.

14. The dental prostheses modeling apparatus of claim 13 wherein said force applying means is further defined as comprising in combination a template including a base having protruding upwardly from an upper surface thereof a lug having an upper surface for abutting a lower surface of said center panel, and a knock-out tool for exerting a downward force on said abutment flanges of said tray relative to said template lug.

* * * * *